(12) United States Patent
Grallert et al.

(10) Patent No.: US 9,063,141 B2
(45) Date of Patent: Jun. 23, 2015

(54) *LISTERIA* BACTERIOPHAGE TAILSPIKE PROTEIN AND USES THEREOF

(75) Inventors: Holger Grallert, Weilheim (DE); Sonja Molinaro, Weilheim (DE); Julia Lorenz, Regensburg (DE)

(73) Assignee: BIOMERIEUX SA, Marcy l'Etoile (FR)

( * ) Notice: Subject to any disclaimer, the term of this patent is extended or adjusted under 35 U.S.C. 154(b) by 0 days.

(21) Appl. No.: 14/118,925

(22) PCT Filed: May 29, 2012

(86) PCT No.: PCT/EP2012/002266
§ 371 (c)(1),
(2), (4) Date: Feb. 13, 2014

(87) PCT Pub. No.: WO2012/159772
PCT Pub. Date: Nov. 29, 2012

(65) Prior Publication Data
US 2014/0302495 A1 Oct. 9, 2014

(30) Foreign Application Priority Data
May 26, 2011 (EP) .................................... 11004347

(51) Int. Cl.
A61K 39/02 (2006.01)
A61K 39/00 (2006.01)
C07H 21/04 (2006.01)
G01N 33/569 (2006.01)
C07K 14/01 (2006.01)
C07K 14/005 (2006.01)

(52) U.S. Cl.
CPC .......... *G01N 33/56911* (2013.01); *A61K 39/00* (2013.01); *C12N 2795/00033* (2013.01); *C07K 14/01* (2013.01); *C12N 2795/00071* (2013.01); *C07K 14/005* (2013.01)

(58) Field of Classification Search
CPC ......... A61K 39/00; A61K 39/02; C12Q 1/00; C07H 21/04
USPC .......... 424/184.1, 185.1, 190.1, 234.1; 425/4; 536/23.1, 23.7
See application file for complete search history.

(56) References Cited

U.S. PATENT DOCUMENTS

| | | | |
|---|---|---|---|
| 5,252,466 A | 10/1993 | Cronan, Jr. | |
| 5,506,121 A | 4/1996 | Skerra et al. | |
| 5,723,584 A | 3/1998 | Schatz | |
| 5,874,239 A | 2/1999 | Schatz | |
| 5,932,433 A | 8/1999 | Schatz | |
| 7,645,582 B2 | 1/2010 | Yamamoto et al. | |

FOREIGN PATENT DOCUMENTS

| | | |
|---|---|---|
| EP | 0 511 747 | 11/1992 |
| WO | WO 2008/077397 | 7/2008 |
| WO | WO 2008/121830 | 10/2008 |
| WO | WO 2012/159774 | 11/2012 |

OTHER PUBLICATIONS

Andres et al., "Trailspike interactions with lipopolysaccharide effect DNA ejection from phage P22 particles in vitro," *Journal of Biological Chemistry*, 285(47):36768-36775, 2010.

Goldfine and Knob, "Purification and characterization of *Listeria monocytogenes* phosphatidylinositol-specific phospholipase C," *Infection and Immunity*, 60(10):4059-4067, 1992.

Hagens and Loessner "Application of bacteriophages for detection and control of foodborne pathogens," *Appl. Microbiol. Biotechnol.* 76(3):513-519, 2007.

Handa et al., "Recognition of *Salmonella typhimurium* by Immobilized Phage P22 Monolayers," *Surfaces Science*, 602(7):1392-1400, 2008.

J. Mengaud et al., "Identification of phosphatidylinositol-specific phospholipase C activity in *Listeria monocytogenes*: a novel type of virulence factor?" *Mol. Microbiol.*, 5(2):367-372, 1991.

Leimeister-Wächter et al., "Detection of a gene encoding a phosphatidylinositol-specific phospholipase C that is co-ordinately expressed with listeriolysin in *Listeria monocytogenes*," *Mol. Microbiol.*, 5(2):361-366, 1991.

PCT International Search Report and Written Opinion issued in International Patent Application No. PCT/EP2012/002266, dated Sep. 7, 2012.

Skerra and Schmidt, "Applications of a peptide ligand for streptavidin: the Strep-tag," *Biomolecular Engineering*, 16:79-86, 1999.

*Primary Examiner* — Rodney P Swartz
(74) *Attorney, Agent, or Firm* — Parker Highlander PLLC

(57) ABSTRACT

The present invention relates to a novel tail spike protein (TSP) encoded by the novel *Listeria* bacteriophage designated ProCC P825 and uses of the novel TSP for identifying, detecting and monitoring of *Listeria*.

18 Claims, 2 Drawing Sheets

LISTERIA BACTERIOPHAGE TAILSPIKE PROTEIN AND USES THEREOF

This application is a national phase application under 35 U.S.C. §371 of International Application No. PCT/EP2012/002266, filed May 29, 2012, which claims priority to European Application No. 11 004 347.8, filed May 26, 2011. The entire text of each of the above referenced disclosures is specifically incorporated herein by reference.

The present invention relates to a novel tailspike protein (TSP) encoded by the novel *Listeria*-specific bacteriophage ProCC P825 and uses of the novel TSP for identifying, detecting, and/or monitoring *Listeria*.

BACKGROUND

The gram-positive bacterium *Listeria monocytogenes* is a bacterial pathogen which is known as the causative organism in several food-related outbreaks, illnesses and deaths. Listeriosis is a life-threatening infection of humans worldwide which is caused by *Listeria monocytogenes* and which is characterized by a variety of symptoms and conditions, including diarrhea, abortion and encephalitis. In industrialized countries, high mortality is associated with listeriosis following *Listeria monocytogenes* food contamination. In humans, the prevalence of listeriosis has risen significantly since the 1980s, resulting in intensified surveillance of *Listeria monocytogenes* in food industry. This contributed to a decrease of human listeriosis cases in the last two decades (McLauchlin 1987, Oevermann et al. 2008). However, its prevalence has again increased in the last few years (Gillespie et al. 2006, Goulet et al. 2008, Gillespie et al. 2009).

The species *Listeria monocytogenes* encompasses numerous strains and the genetic diversity amongst them is high (Doumith et al. 2004). Various strains have been implicated in both human and animal disease, and current surveillance schemes for foods are based on the assumption that all *Listeria monocytogenes* isolates are potentially pathogenic, resulting in costly recalls in food industry (Oevermann et al. 2010).

There is increasing public concern for food and water safety. The food safety and human diagnostics markets are in need of faster working, reliable, sensitive, specific, low cost bioassays and biosensors for *Listeria* bacterial detection.

Bacteriophages are viruses that infect bacteria. They are obligate intracellular parasites and lack their own metabolism. Phages are the natural enemies of bacteria. They are host-specific in that they infect specific bacterial species or even specific strains (Hagens and Loessner 2007). The extreme specificity of phages renders them ideal candidates for applications designed to increase food safety. Phages can be used for detection and monitoring of bacteria without interfering with the natural microflora.

It is an object of the present invention to provide bacteriophage-based means and methods for specifically and selectively identifying, detecting and/or monitoring *Listeria*.

SUMMARY OF THE INVENTION

*Listeria*-specific phages have two kinds of binding proteins: the cell binding domain (CBD) of the endolysins, which are required for release of new phage particles from the host cell at the end of the lytic infection cycle, and receptor binding proteins (RBPs), which are required at the beginning of the infection for adsorption of the phage to the host. Here, the terms receptor binding protein (RBP) and tailspike protein (TSP) are used synonymously, wherein the latter term TSP is more commonly used in the related technical field. TSPs recognize and bind to a receptor on the bacterial surface of the host.

The sequence listing that is contained in the file named "GRUNP0005US_ST25.txt", which is 4 KB (as measured in Microsoft Windows®) and was created on Nov. 7, 2013, is filed herewith by electronic submission and is incorporated by reference herein.

The present invention provides a novel tailspike protein (TSP) encoded by the novel *Listeria*-specific bacteriophage ProCC P825 and uses of the novel TSP for the detection and monitoring of *Listeria*. The novel *Listeria* bacteriophage designated ProCC P825, has been deposited at DSMZ, Braunschweig, Germany, under international deposit number DSMZ 23783 in accordance with the Budapest treaty for deposit of cell cultures. The novel bacteriophage "ProCC P825" is simply named "P825". Therefore, whenever reference is made herein to "P825", the novel bacteriophage "ProCC P825" as deposited at DSMZ, Braunschweig, Germany, under deposit number DSMZ 23783 is meant. The novel TSP provided by the present invention is named "P825Orf2". Therefore, whenever reference is made herein to "P825Orf2", the novel TSP in accordance with the present invention is meant.

The novel TSP "P825Orf2" provided by the present invention has been shown to be a reliable, and sensitive tool for specifically and selectively detecting and monitoring *Listeria*.

The novel TSP "P825Orf2" provided by the present invention is encoded by the nucleic acid sequence shown in SEQ ID NO: 1, which comprises 1,896 nucleotides. The corresponding amino acid sequence of P825Orf2 is set forth in SEQ ID NO: 2 and comprises 632 amino acid residues accordingly. The novel TSP "P825Orf2" provided by the present invention is particularly useful for identifying, detecting and/or monitoring *Listeria*.

Aspects of the invention are:

1. A nucleic acid molecule comprising a polynucleotide selected from the group consisting of:

(a) a polynucleotide encoding a polypeptide having the amino acid sequence of SEQ ID NO: 2;

(b) a polynucleotide encoding a fragment, analog or functional derivative of a polypeptide encoded by the polynucleotide of (a), wherein said fragment, analog or functional derivative has binding specificity for *Listeria* cells;

(c) a polynucleotide which is at least 75% identical to the polynucleotide of (a), and which encodes a polypeptide having binding specificity for *Listeria* cells;

(d) a polynucleotide encoding a polypeptide having an amino acid sequence that is at least 75% identical to the amino acid sequence of SEQ ID NO: 2 and having binding specificity for *Listeria* cells;

(e) a polynucleotide which hybridizes under stringent conditions to the polynucleotide of any one of (a) to (d);

(f) a polynucleotide comprising the nucleotide sequence of SEQ ID NO: 1;

(g) a polynucleotide which is at least 75% identical to the nucleotide sequence of SEQ ID NO: 1 and which encodes a polypeptide having binding specificity for *Listeria* cells;

(h) a polynucleotide comprising part of the nucleotide sequence of (f) and which encodes a fragment, analog or functional derivative of the polypeptide having the amino acid sequence of SEQ ID NO: 2, wherein said fragment, analog or functional derivative has binding specificity for *Listeria* cells; and (i) a polynucleotide that is the complement of the full length of a polynucleotide of any of (a) to (h).

2. A vector comprising the nucleic acid molecule of item 1.
3. A host cell transformed or transfected with the nucleic acid molecule of item 1, or the vector of item 2.
4. The host cell of item 3, containing a polypeptide expressed from the nucleic acid molecule of item 1, or from the vector of item 2.
5. A method of making a polypeptide encoded by the nucleic acid molecule of item 1, comprising culturing the host cell of item 3 under conditions such that the polypeptide encoded by the nucleic acid molecule of item 1 is expressed, and recovering the polypeptide encoded by said nucleic acid molecule.
6. A polypeptide encoded by the nucleic acid molecule of item 1, or obtainable by the method of item 5.
7. A tailspike protein obtainable from bacteriophage ProCC P825 deposited under accession No. DSMZ 23783, or a fragment, analog or functional derivative thereof having binding specificity for *Listeria* cells.
8. A chimeric protein comprising the polypeptide of item 6 or the tailspike protein of item 7 and a heterologous protein, wherein the chimeric protein has binding specificity for *Listeria* cells.
9. A composition, preferably a diagnostic composition, comprising (i) the nucleic acid molecule of item 1, (ii) the vector of item 2, (iii) the host cell of item 3 or 4, (iv) the polypeptide of item 6, (v) the tailspike protein of item 7, or (vi) the chimeric protein of item 8.
10. A method of detecting *Listeria* in a sample comprising contacting a sample suspected to contain *Listeria* with the polypeptide of item 6, the tailspike protein of item 7, the chimeric protein of item 8, or the composition of item 9.
11. Use of the nucleic acid molecule of item 1, the vector of item 2, the host cell of item 3 or 4, the polypeptide of item 6, the tailspike protein of item 7, or the chimeric protein of item 8 in a method of detecting *Listeria* in a sample suspected to contain *Listeria*.
12. The method of item 10, or the use of item 11, wherein the method of detecting *Listeria* is an in vitro method of detecting *Listeria* infection in a subject, wherein the method comprises contacting a sample obtained from the subject and suspected to contain *Listeria* with the polypeptide of item 6, the tailspike protein of item 7, the chimeric protein of item 8, or the composition of item 9.
13. A kit for detecting *Listeria* in sample suspected to contain *Listeria* comprising the nucleic acid molecule of item 1, the vector of item 2, the host cell of item 3 or 4, the polypeptide of item 6, the tailspike protein of item 7, or the chimeric protein of item 8.
14. The method of item 10 or 12, or the use of item 11 or 12, or the kit of item 13, wherein the polypeptide of item 6, the tailspike protein of item 7, and the chimeric protein of item 8, respectively, is immobilized to a solid support.
15. An antibody or fragment thereof that binds specifically to the polypeptide of item 6, the tailspike protein of item 7, or the chimeric protein of item 8.

DETAILED DESCRIPTION OF THE INVENTION

The novel *Listeria*-specific bacteriophage designated ProCC P825 ("P825") has been deposited internationally on Jul. 14, 2010 at the DSMZ—Deutsche Sammlung von Mikroorganismen und Zellkulturen GmbH, Braunschweig, Germany, under international deposit accession No. DSM No. 23783 in accordance with the Budapest treaty for deposit of cell cultures. The address of DSMZ is as follows: Inhoffenstr. 7B, 38124 Braunschweig, Germany.

The name and address of the depositor of the novel bacteriophage P825 is as follows: Hyglos Invest GmbH, Am Neuland 1, 82347 Bernried, Germany. Evidence is provided by a separate document enclosed with this application that the depositor Hyglos Invest GmbH, Bernried, Germany, has authorized the applicant to refer to the deposited biological material in the present application, and has given his unreserved and irrevocable consent to the deposited material being made available to the public (in accordance with, for example, Rule 33 EPC). In addition, said separate document provides evidence that the depositor Hyglos Invest GmbH, Bernried, Germany, has given his consent that the applicant makes use of the so-called "expert solution" (in accordance with, for example, Rule 32 EPC).

The phage P825 exhibits lytic activity against *Listeria* bacteria. Phage P825 not only completely inhibits growth of *Listeria* strains but actually reduces *Listeria* titers. As confirmed by enrichment studies, applying phage P825 completely eradicated *Listeria* bacteria. The lysis spectrum of phage P825 has been shown to be consistent with the binding specificity provided by the tailspike protein (TSP) "P825Orf2" of phage P825.

Figure 1:
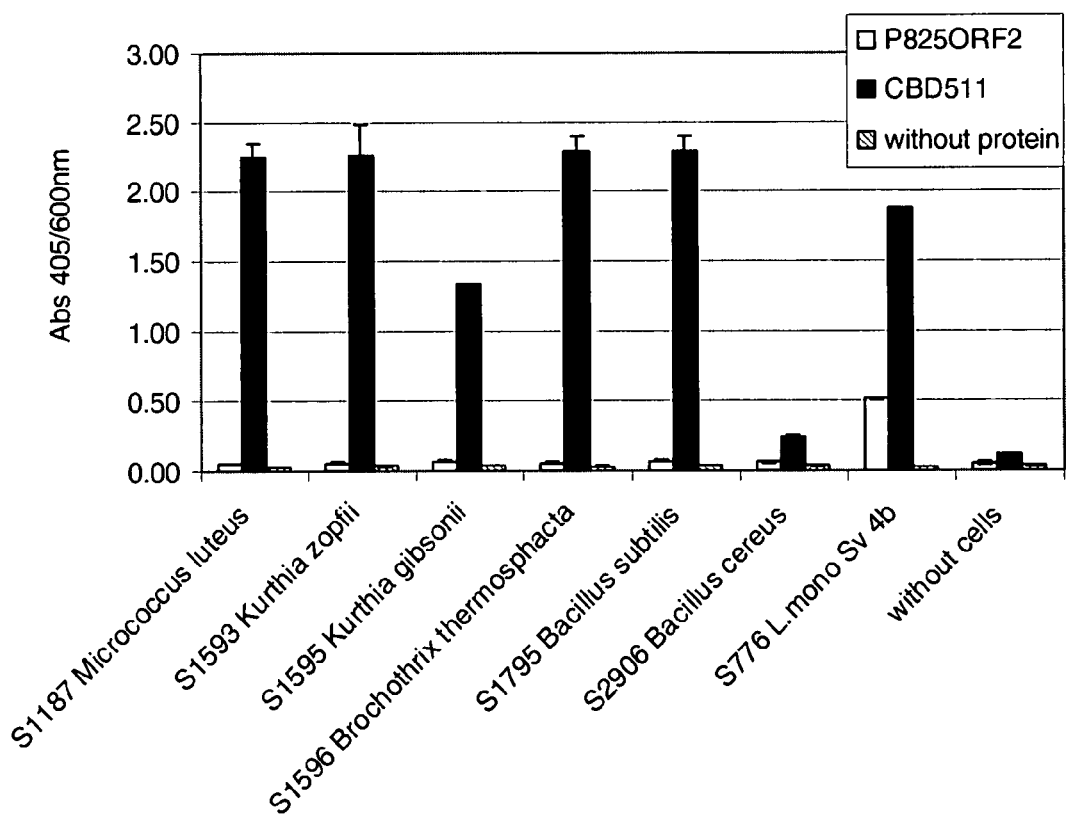
FIG. 1 shows specificity of P825Orf2. Exclusivity testing was performed by comparison of binding of HisJS-P825Orf2 and CBD511 (i.e., the cell wall binding domain of the known endolysin Ply511 from known *Listeria* bacteriophage A511) against *Listeria* and non-*Listeria* strains. L. mono means *Listeria monocytogenes*.
Figure 2:
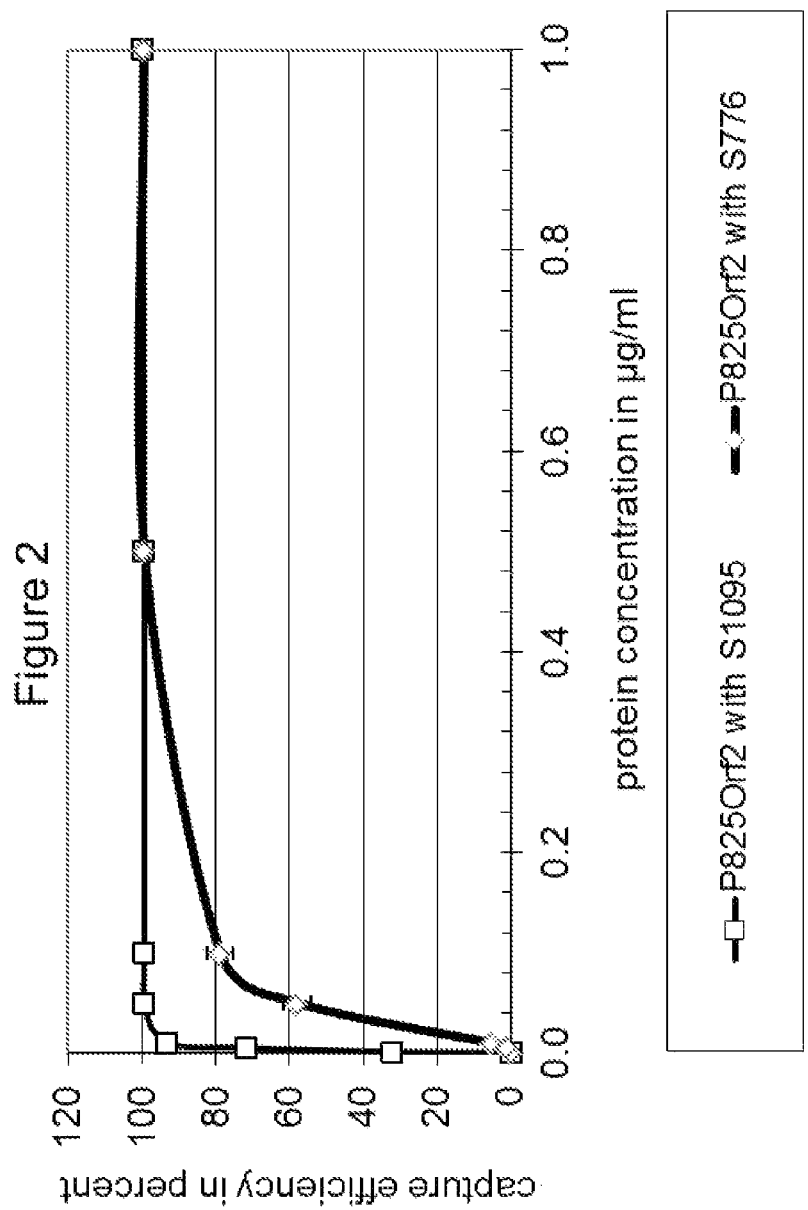
FIG. 2 shows affinity testing of in vivo biotinylated *Listeria* phage TSP HisJS-P825Orf2. Protein concentrations from 0.001 µg/ml to 1 µg/ml were used in the test. For control of unspecific binding, a test without protein was included.

The inventors of the present application have demonstrated that the novel *Listeria* bacteriophage TSP "P825Orf2" is highly specific for *Listeria* bacteria and exhibits a superior capture efficiency for *Listeria* bacteria (FIGS. 1 and 2). Therefore, *Listeria* bacterial cells or cell components may be enriched selectively with methods provided by the present invention, which make use of the novel *Listeria* TSP "P825Orf2". Specifically, *Listeria* bacterial cells or cell components may be enriched selectively from mixed cell cultures of different genera and species, or from a culture of a single species. The use of the novel TSP provided by the present invention provides for the selectivity and specificity of the methods provided by the present invention.

The novel TSP provided by the present invention recognizes its host bacteria in a highly specific manner and with high binding affinity.

The *Listeria*-specific bacteriophage ProCC P825 ("P825") has been deposited internationally on Jul. 14, 2010 at DSMZ (Deutsche Sammlung von Mikroorganismen und Zellkulturen GmbH, Braunschweig, Germany) under international deposit accession No. DSMZ No. 23783 in accordance with the Budapest treaty concerning deposit of cell cultures.

P825Orf2 Nucleic Acid and Amino Acid Sequences and Variants Thereof

The present invention provides a nucleic acid molecule comprising a polynucleotide encoding a polypeptide having the amino acid sequence of SEQ ID NO: 2. The present invention also provides a nucleic acid molecule, which comprises a polynucleotide that is at least 75% or at least 80% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2. The present invention further provides a nucleic acid molecule, which comprises a polynucleotide that is at least 85% or at least 90% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2. In various embodiments, the said nucleic acid molecule comprises a polynucleotide that is at least 91% or at least 92% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2. Preferably, the said nucleic acid molecule comprises a polynucleotide that is at least 93% or at least 94% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2. More preferably, the said nucleic acid molecule comprises a polynucleotide that is at least 95% or at least 96% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2. Still more preferably, the said nucleic acid molecule comprises a polynucleotide that is at least 97%, at least 98%, or even at least 99% identical to a polynucleotide encoding a polypeptide having the amino acid sequence of SEQ ID NO: 2, and that encodes a polypeptide having binding specificity for *Listeria* cells, preferably the specificity of the TSP of SEQ ID NO: 2.

Furthermore, the present invention provides a nucleic acid molecule comprising a polynucleotide, which encodes a polypeptide having an amino acid sequence that is at least 75% or at least 80% identical to the amino acid sequence of SEQ ID NO: 2, and which has binding specificity for *Listeria* cells, preferably the specificity of the TSP of SEQ ID NO: 2. The present invention also provides a nucleic acid molecule comprising a polynucleotide, which encodes a polypeptide having an amino acid sequence that is at least 85% or at least 90% identical to the amino acid sequence of SEQ ID NO: 2, and which has binding specificity for *Listeria* cells, preferably the specificity of the TSP of SEQ ID NO: 2. In various embodiments, the said nucleic acid molecule comprises a polynucleotide, which encodes a polypeptide having an amino acid sequence that is at least 91% or at least 92% identical to the amino acid sequence of SEQ ID NO: 2, and which has binding specificity for *Listeria* cells, preferably the specificity of the TSP of SEQ ID NO: 2. Preferably, the said nucleic acid molecule comprises a polynucleotide, which encodes a polypeptide having an amino acid sequence that is at least 93% or at least 94% identical to the amino acid sequence of SEQ ID NO: 2, and which has binding specificity for *Listeria* cells, preferably the specificity of the TSP of SEQ ID NO: 2. More preferably, the said nucleic acid molecule comprises a polynucleotide, which encodes a polypeptide having an amino acid sequence that is at least 95% or at least 96% identical to the amino acid sequence of SEQ ID NO: 2, and which has binding specificity for *Listeria* cells, preferably the specificity of the TSP of SEQ ID NO: 2. Still more preferably, the said nucleic acid molecule comprises a polynucleotide, which encodes a polypeptide having an amino acid sequence that is at least 97%, at least 98%, or even 99% identical to the amino acid sequence of SEQ ID NO: 2, and which has binding specificity for *Listeria* cells, preferably the specificity of the TSP of SEQ ID NO: 2. Furthermore, the present invention provides a nucleic acid molecule comprising a polynucleotide, which encodes a fragment, analog or functional derivative of a polypeptide encoded by a polynucleotide encoding a polypeptide having the amino acid sequence of SEQ ID NO: 2, wherein said fragment, analog or functional derivative has binding specificity for *Listeria* cells, preferably the specificity of the TSP of SEQ ID NO: 2. Preferably, the said nucleic acid molecule comprises a polynucleotide, which encodes a fragment, analog or functional derivative of a polypeptide encoded by the polynucleotide of SEQ ID NO: 1, wherein said fragment, analog or functional derivative has binding specificity for *Listeria* cells, preferably the specificity of the TSP of SEQ ID NO: 2.

The present invention provides a nucleic acid molecule comprising a polynucleotide, which hybridizes under stringent conditions to any one of the polynucleotides described in the three preceding paragraphs. The present invention also provides a nucleic acid molecule comprising a polynucleotide that is the complement of the full-length of any one of the polynucleotides described in the three preceding paragraphs.

The present invention provides a nucleic acid molecule comprising a polynucleotide having the nucleotide sequence of SEQ ID NO: 1. The present invention also provides a nucleic acid molecule, which comprises a polynucleotide that is at least 75% or at least 80% identical to the nucleotide sequence of SEQ ID NO: 1, and that encodes a polypeptide having binding specificity for *Listeria* cells, preferably the specificity of the TSP of SEQ ID NO: 2. The present invention further provides a nucleic acid molecule, which comprises a polynucleotide that is at least 85% or at least 90% identical to the nucleotide sequence of SEQ ID NO: 1, and that encodes a polypeptide having binding specificity for *Listeria* cells, preferably the specificity of the TSP of SEQ ID NO: 2. In various embodiments, the said nucleic acid molecule comprises a polynucleotide that is at least 91% or at least 92% identical to the nucleotide sequence of SEQ ID NO: 1, and that encodes a polypeptide having binding specificity for *Listeria* cells, preferably the specificity of the TSP of SEQ ID NO: 2. Preferably, the said nucleic acid molecule comprises a polynucleotide that is at least 93% or at least 94% identical to the nucleotide sequence of SEQ ID NO: 1, and that encodes a polypeptide having binding specificity for *Listeria* cells, preferably the specificity of the TSP of SEQ ID NO: 2. More preferably, the said nucleic acid molecule comprises a polynucleotide that is at least 95% or at least 96% identical to the nucleotide sequence of SEQ ID NO: 1, and that encodes a polypeptide having binding specificity for *Listeria* cells, preferably the specificity of the TSP of SEQ ID NO: 2. Still more preferably, the said nucleic acid molecule comprises a polynucleotide that is at least 97%, at least 98%, or even at least 99% identical to the nucleotide sequence of SEQ ID NO: 1, and that encodes a polypeptide having binding specificity for *Listeria* cells, preferably the specificity of the TSP of SEQ ID NO: 2.

Furthermore, the present invention provides a nucleic acid molecule comprising a polynucleotide that is a part of the nucleotide sequence of SEQ ID NO: 1, and that encodes a fragment, analog or functional derivative of the polypeptide having the amino acid sequence of SEQ ID NO: 2, wherein said fragment, analog or functional derivative has binding specificity for *Listeria* cells, preferably the specificity of the TSP of SEQ ID NO: 2.

The present invention provides a nucleic acid molecule comprising a polynucleotide, which hybridizes under stringent conditions to any one of the polynucleotides described in the two preceding paragraphs. Preferably, the present invention provides a nucleic acid molecule comprising a polynucleotide, which hybridizes under stringent conditions to the polynucleotide of SEQ ID NO: 1. The present invention also provides a nucleic acid molecule comprising a polynucleotide that is the complement of the full-length of any one of the polynucleotides described in the two preceding paragraphs. Preferably the present invention provides a nucleic acid molecule comprising a polynucleotide that is the complement of the full-length of the polynucleotide of SEQ ID NO: 1.

As used herein, a nucleic acid molecule of the present invention is DNA or RNA.

Vectors and Host Cells

The present invention provides recombinant vectors containing nucleic acid molecules of the present invention. In various embodiments, provided is a single recombinant vector containing a single nucleic acid molecule of the present invention. In various other embodiments, provided is a single recombinant vector containing several nucleic acid molecules of the present invention. In still other embodiments, provided are several recombinant vectors each containing a single nucleic acid molecule of the present invention. In still further embodiments, provided are several recombinant vectors each containing several nucleic acid molecules of the present invention.

In various embodiments, the nucleic acid molecule or nucleic acid molecules contained in a single or several vectors according to the present invention are operatively linked to an expression control sequence allowing expression of the polynucleotide or polynucleotides in prokaryotic or eukaryotic host cells. Preferably, the expression control sequence is a promoter or a promoter sequence. Suitable promoters are known to the skilled artisan. In various embodiments, the vector is a plasmid. Other suitable vectors will be readily apparent to the skilled artisan. A recombinant vector according to the present invention may also be called expression vector or expression construct.

The expression constructs according to the present invention may further contain sites for transcription initiation, termination and, in the transcribed region, a ribosome binding site for translation. The coding portion of the TSP of the transcripts expressed by the constructs according to the present invention will preferably include a translation initiating codon at the beginning and a termination codon (UAA, UGA or UAG) appropriately positioned at the end of the polypeptide to be translated.

In various embodiments, the expression vectors according to the present invention will include at least one selectable marker. Suitable selection markers are known to the skilled artisan.

The present invention provides a method of making a recombinant vector comprising inserting a nucleic acid molecule of the present invention into a vector.

The present invention also provides a method of making a recombinant host cell comprising introducing a nucleic acid molecule or a recombinant vector according to the present invention into a host cell.

The present invention also provides a host cell genetically engineered with a nucleic acid molecule or a recombinant vector according to the present invention. In various embodiments, "genetically engineered" means that the host cell is transformed or transfected with a nucleic acid molecule or a recombinant vector according to the present invention. In various embodiments, the genetically engineered host cell according to the present invention contains a polypeptide expressed from a nucleic acid molecule or from a recombinant vector in accordance with the present invention. Representative examples of appropriate host cells include, but are not limited to, bacterial cells such as *E. coli* cells, fungal cells such as yeast cells, insect cells such as *Drosophila* S2 and *Spodoptera* Sf9 cells, animal cells such as CHO, COS, and HEK293 cells, and plant cells. Appropriate culture mediums and conditions for host cells of the present invention are known in the art.

Proteins/Polypeptides

The present invention provides a protein or polypeptide comprising the amino acid sequence of SEQ ID NO: 2. The present invention also provides a protein or polypeptide comprising and amino acid sequence that is at least 75% or at least 80% identical to the amino acid sequence of SEQ ID NO: 2, wherein the protein or polypeptide has binding specificity for *Listeria* cells, preferably the specificity of the TSP of SEQ ID NO: 2. The present invention further provides a protein or polypeptide, which comprises an amino acid sequence that is at least 85% or at least 90% identical to the amino acid sequence of SEQ ID NO: 2, wherein the protein or polypeptide has binding specificity for *Listeria* cells, preferably the specificity of the TSP of SEQ ID NO: 2. In various embodiments, the said polypeptide comprises an amino acid sequence that is at least 91% or at least 92% identical to the amino acid sequence of SEQ ID NO: 2, wherein the protein or polypeptide has binding specificity for *Listeria* cells, preferably the specificity of the TSP of SEQ ID NO: 2. Preferably, the said protein or polypeptide comprises an amino acid sequence that is at least 93% or at least 94% identical to the amino acid sequence of SEQ ID NO: 2, wherein the protein or polypeptide has binding specificity for *Listeria* cells, preferably the specificity of the TSP of SEQ ID NO: 2. More preferably, the said protein or polypeptide comprises an amino acid sequence that is at least 95% or at least 96% identical to the amino acid sequence of SEQ ID NO: 2, wherein the protein or polypeptide has binding specificity for *Listeria* cells, preferably the specificity of the TSP of SEQ ID NO: 2. Still more preferably, the said protein or polypeptide comprises an amino acid sequence that is at least 97%, at least 98%, or even at least 99% identical to the amino acid sequence of SEQ ID NO: 2, wherein the protein or polypeptide has binding specificity for *Listeria* cells, preferably the specificity of the TSP of SEQ ID NO: 2. In various embodiments, the present invention provides a protein or polypeptide, which encodes a fragment, analog or functional derivative of the protein or polypeptide having the amino acid sequence of SEQ ID NO: 2, wherein said fragment, analog or functional derivative has binding specificity for *Listeria* cells, preferably the specificity of the TSP of SEQ ID NO: 2. In various embodiments, the present inventions provides a protein or polypeptide, which encodes a fragment, analog or functional derivative of the variant proteins or variant polypeptides described above, i.e., the variant proteins or variant polypeptides, which are defined by amino acid sequence identity to the protein or polypeptide comprising the amino acid sequence of SEQ ID NO: 2.

Recombinant proteins of the present invention can be isolated and purified from a host cell of the present invention containing or expressing the proteins/polypeptides by techniques known in the art including, but not limited to, lysis, chromatography, filtration, and centrifugation. In various embodiments, the proteins or polypeptides according to the present invention, including, but not limited to, recombinant, isolated and/or purified proteins or polypeptides, are labeled. Preferably, the label is selected from the group consisting of an enzyme label, a radioisotope, a dye label, colloidal gold and biotin.

In various embodiments, a protein or polypeptide according to the present invention is a purified protein or polypeptide.

A protein of the present invention having binding specificity for *Listeria* cells, preferably the P825Orf2 tailspike protein, can be isolated from the host cell prior to administration in any methods according to the present invention, or the host cell containing the recombinant protein can be directly used in methods according to the present invention without prior isolation of the protein having binding specificity for *Listeria* cells. For example, a host bacterium, which produces the P825Orf2 tailspike protein of the present invention can be applied in methods of identifying, detecting, and/or monitoring *Listeria* according to the present invention where the P825Orf2 tailspike protein would be secreted, for example, into food or foodstuff, onto a surface or in the gut of a subject. The P825Orf2 tailspike protein of the present invention can then bind to *Listeria* cells present in such an environment, and *Listeria* binding can be determined accordingly.

The present invention also provides a method of making a polypeptide of the present invention encoded by a nucleic acid molecule of the present invention, wherein the method comprises (i) culturing a genetically engineered host cell of the present invention under conditions such that the polypeptide encoded by a nucleic acid molecule of the present invention is expressed, and (ii) recovering the polypeptide encoded by the nucleic acid molecule. The polypeptide may be expressed in a modified form, such as a fusion protein, and may include not only secretion signals, but also additional heterologous functional regions. For example, a region of additional amino acids, particularly charged amino acids, may be added to the N-terminus of the polypeptide to improve stability and persistence in the host cell, during purification, or during subsequent handling and storage of the polypeptide. Also, peptide moieties may be added to the polypeptide to facilitate purification. Such regions may be removed prior to final preparation of the polypeptide. The addition of peptide moieties to polypeptides of the present invention for, inter alia, inducing secretion, improving stability and/or facilitating purification are familiar to the ones of ordinary skill and belong to routine techniques in the art. A preferred fusion protein comprises a heterologous region from an immunoglobulin that is useful to stabilize and purify proteins.

As one of skill in the art will appreciate, polypeptides of the present invention can be combined with parts of the constant domain of immunoglobulins (IgG), resulting in chimeric polypeptides. These fusion proteins may facilitate purification and may show an increased half-life in vivo.

For many proteins it is known in the art that one or more amino acids may be deleted from the N-terminus or C-terminus without substantial loss of biological function or activity. Here, biological function/activity includes any function and activity of the proteins of the present invention described herein including, but not limited to, any lytic function/activity and cell wall binding function/activity described herein.

The present invention provides polypeptides encoded by the nucleic acid molecules of the present invention. The present invention also provides polypeptides obtainable by methods of making the polypeptides according to the present invention. Therefore, the present invention encompasses and provides each polypeptide that is encoded by any nucleic acid molecule of the present invention. Furthermore, the present invention encompasses and provides each polypeptide that is obtainable by any method of making the polypeptide according to the present invention.

Proteins and polypeptides of the present invention also encompass chimeric proteins and polypeptides according to the present invention, and combinations of the TSP of the present invention with known cell wall binding domains according to the present invention.

Antibodies

The present invention also provides an antibody or fragment thereof that binds specifically to a polypeptide of the present invention. Preferably, the antibody specifically binds to the full-length polypeptide having the amino acid sequence of SEQ ID NO: 2.

In various embodiments, the antibody of the present invention is selected from the group consisting of a monoclonal antibody, a polyclonal antibody, a chimeric antibody, a Fab fragment, a F(ab')$_2$ fragment, and a scFv fragment. In various embodiments, the antibody according to the present invention is labeled. Preferably, the label is selected from the group consisting of an enzyme label, a radioisotope, a fluorescent label, and biotin. The polypeptides of the present invention can be used to raise polyclonal and monoclonal antibodies provided by the present invention. The antibodies of the present invention may be prepared by any of a variety of methods available in the art and known to the skilled artisan.

The antibody fragments provided by the present invention, whether attached to other sequences or not, can also include insertions, deletions, substitutions, or other selected modifications of particular regions or specific amino acids residues, provided the activity of the antibody fragment is not significantly altered or impaired compared to the non-modified antibody or antibody fragment. These modifications can provide for some additional property, such as to remove/add amino acids capable of disulfide bonding. In any case, antibody fragments according to the present invention must possess a bioactive property, such as specific binding to its cognate antigen.

Functional or active regions of the antibodies or antibody fragments of the present invention may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

Chimeric Proteins

The present invention further provides a chimeric protein comprising a TSP according to the present invention and one or more heterologous proteins. Preferably, the chimeric protein of the present invention has binding specificity for *Listeria* cells. More preferably, the chimeric protein has the binding specificity of the polypeptide of SEQ ID NO: 2.

In various embodiments, the chimeric proteins according to the present invention comprise more than one protein of the present invention. That is, the chimeric proteins according to the present invention may comprise tandem repeats of a protein of the present invention.

In various embodiments, the chimeric proteins according to the present invention comprise tandem repeats of the one or more heterologous proteins.

In the present invention, the term "fusion protein(s)" may be used synonymously for the term "chimeric protein(s)".

Compositions and Solutions

The present invention provides compositions comprising combinations of proteins as described herein above. Specifically, such a combination is the combination of a TSP of the present invention with one or more cell wall binding domains of known endolysins from other known *Listeria* bacteriophages as described herein above. Furthermore, such a combination is particularly the combination of a TSP of the present invention with one or more cell wall binding domains of known autolysins as described herein above. Such a combination is also particularly the combination of a TSP of the present invention with one or more cell wall binding domains of known bacteriocins as described herein above.

The present invention also provides compositions comprising chimeric proteins according to the present invention. In general, the present invention provides a composition comprising a TSP according to the present invention. The present invention also provides a composition comprising a nucleic acid molecule or a vector according to the present invention. The present invention further provides a composition comprising a host cell according to the present invention. The present invention further provides a composition comprising a chimeric protein according to the present invention.

In various embodiments, a composition according to the present invention is a diagnostic composition.

In various embodiments, a composition according to the present invention is a cleaning composition.

The present invention provides solutions, preferably diagnostic or cleaning solutions, comprising combinations of proteins of the invention as described herein above. Specifically, such a combination is the combination of a TSP of the present invention with one or more cell wall binding domains of known endolysins from other known *Listeria* bacteriophages as described herein above. Furthermore, such a combination is particularly the combination of a TSP of the present invention with one or more cell wall binding domains of known autolysins as described herein above. Such a combination is also particularly the combination of a TSP of the present invention with one or more cell wall binding domains of known bacteriocins as described herein above.

The present invention also provides solutions, preferably diagnostic or cleaning solutions, comprising chimeric proteins according to the present invention. In general, the present invention provides a solution, preferably a diagnostic solution, comprising a TSP according to the present invention. The present invention also provides a solution, preferably a diagnostic solution, comprising a nucleic acid molecule or a vector according to the present invention. The present invention further provides a solution, preferably a diagnostic solution, comprising a host cell according to the present invention.

Methods for Identifying, Detecting, and/or Monitoring *Listeria*

The present invention provides a method for identifying *Listeria*, comprising contacting a sample suspected to contain *Listeria* with a protein or composition according to the present invention, with the proviso that the method is not a therapeutic method. In various embodiments, the in vitro method for identifying *Listeria* according to the present invention comprising contacting a sample suspected to contain *Listeria* with a nucleic acid molecule of the present invention, a vector of the present invention, or a host cell of the present invention.

The present invention provides an in vitro method for detecting *Listeria*, comprising contacting a sample suspected to contain *Listeria* with a protein or composition according to the present invention. In various embodiments, the in vitro method for detecting *Listeria* according to the present invention comprising contacting a sample suspected to contain *Listeria* with a nucleic acid molecule of the present invention, a vector of the present invention, or a host cell of the present invention.

The present invention provides an in vitro method for monitoring *Listeria*, comprising contacting a sample suspected to contain *Listeria* with a protein or composition according to the present invention. In various embodiments, the in vitro method for monitoring *Listeria* according to the present invention comprising contacting a sample suspected to contain *Listeria* with a nucleic acid molecule of the present invention, a vector of the present invention, or a host cell of the present invention.

The present invention provides a composition or solution according to the present invention for use in diagnosis or diagnostic purposes (diagnostics), with the proviso that the diagnosis or diagnostics are not practiced on the human or animal body.

The present invention provides the TSP P825Orf2 for use in diagnosis or diagnostic purposes (diagnostics), with the proviso that the diagnosis or diagnostics are not practiced on the human or animal body.

In various embodiments, "identifying *Listeria*" according to the present invention means "identifying *Listeria* contamination". Preferably, identifying *Listeria* contamination means identifying undesired colonization of *Listeria* bacteria.

In various embodiments, "detecting *Listeria*" according to the present invention means "detecting *Listeria* contamination". Preferably, identifying *Listeria* contamination means detecting undesired colonization of *Listeria* bacteria.

In various embodiments, "monitoring *Listeria*" according to the present invention means "monitoring *Listeria* contamination". Preferably, monitoring *Listeria* contamination means monitoring undesired colonization of *Listeria* bacteria.

As used herein, "*Listeria* contamination" means "undesired *Listeria* contamination". In the present invention, undesired *Listeria* contamination includes, but is not limited to, contamination of pathogenic and non-pathogenic *Listeria* bacteria. Here, pathogenic means exhibiting pathogenicity to human beings and/or animals. *Listeria monocytogenes* is pathogenic to both human and animals. Therefore, in the present invention identifying *Listeria* contamination is preferably identifying *Listeria monocytogenes* contamination. Furthermore, in the present invention detecting *Listeria* contamination is preferably detecting *Listeria monocytogenes* contamination. Therefore, in the present invention identifying *Listeria* contamination preferably is identifying *Listeria monocytogenes* contamination. Still further, in the present invention monitoring *Listeria* contamination is preferably monitoring *Listeria monocytogenes* contamination.

Methods for Purification, Depletion and/or Enrichment of *Listeria* Cells and Cell Components The present invention provides a method for purification, depletion and/or enrichment of *Listeria* cells or *Listeria* cell components, comprising contacting a sample suspected to contain *Listeria* cells or cell components of *Listeria* cells with a protein or composition according to the present invention, with the proviso that the method is not a therapeutic method.

*Listeria* cells or cell wall components can be enriched selectively with methods according to the present invention, including enrichment from mixed cultures of bacteria. Selective enrichment and purification according to the present invention is performed by separating *Listeria* bacteria from a sample or culture, including mixed cultures, using a TSP of the present invention.

In various embodiments, the TSP of the present invention is used for depleting a sample or culture from *Listeria* bacteria. In various embodiments, the TSP of the present invention is used for purifying a sample or culture from *Listeria* bacteria. In various embodiments, the TSP of the present invention is used for enriching *Listeria* from a sample or culture.

The methods of the present invention useful for enrichment and purification of *Listeria* from complex matrices.

The methods of the present invention are useful in any kind of sample preparation including, but not limited to, sample preparation for plating with the aim of identifying *Listeria* bacteria. That is, the TSP of the present invention is particularly useful for pre-enriching *Listeria* bacteria so as to reach cell numbers sufficient for detection in a small test volume. The use of TSPs according to the present invention provides for sample preparations, which are prone to inhibition by interfering sample matter like sample preparations commonly used in the art.

The methods according to the present invention may be performed using a solid support as described herein elsewhere.

Diagnostic Assays

The novel TSP protein of the present invention can be used in assays for detecting the presence of *Listeria*, more specifically *Listeria* bacterial cells or cell components, in test samples in fields such as clinical and forensic medicine, environmental testing, food quality assurance, and related areas. Thus, the present invention provides assays for detecting the presence of *Listeria*, more specifically *Listeria* bacterial cells or cell components, in test samples in fields such as clinical and forensic medicine, environmental testing, food quality assurance, and related areas using a TSP protein of the present invention.

Methods for Identifying or Detecting *Listeria* Infection

Methods for identifying or detecting *Listeria*, preferably *Listeria* contamination, according to the present invention can be used for identifying or detecting a disease or condition caused by *Listeria* infection. Therefore, the present invention provides a method for identifying or detecting a disease or condition caused by *Listeria* infection comprising identifying or detecting *Listeria* using a method or assay according to the present invention. Specifically, the present invention provides a method for identifying or detecting a disease or condition caused by *Listeria* infection comprising identifying or detecting *Listeria* using a protein or composition according to the present invention.

In various embodiments, the disease or condition caused by a *Listeria* infection is listeriosis. Listeriosis is an infection resulting form the ingestion of food or foodstuff contaminated by *Listeria* bacteria. In various embodiments listeriosis is caused by a *Listeria* infection resulting form the ingestion of food or foodstuff contaminated by *Listeria*. Preferably, listeriosis according to the present invention is caused by a *L. monocytogenes* infection resulting form the ingestion of food or foodstuff contaminated by *L. monocytogenes*. In various other embodiments the disease or condition caused by a *Listeria* infection is brain abscess, hepatitis, peritonitis, arthritis, gastroenteritis, encephalitis, sepsis, local wound infection, and inflammation of conjunctiva and cornea. Preferably, the disease or condition caused by a *Listeria* infection is listeriosis.

General Aspects of Methods of the Present Invention

The methods of the present invention comprise application of "means" provided by the present invention. As used herein, "means" of the present invention include, but are not limited to, nucleic acids, proteins and polypeptides, vectors, host cells, compositions and solutions and the like provided by the present invention, including variants of the nucleic acids, proteins/polypeptides, vectors, host cells, compositions and solutions of the present invention as described herein. "Means" according to the present invention also include proteins/polypeptides of the present invention immobilized to a solid support according to the present invention.

The methods provided by the present invention may include a step of providing a sample suspected to contain *Listeria* bacteria according to the present invention.

In various embodiments, the methods of the present invention comprise washing steps where appropriate.

In various embodiments, the methods provided by the present invention may include a step of separation of *Listeria* cells and/or cell components of *Listeria* cells from the sample after the sample has been incubated with a means according to the present invention.

In various embodiments, a sample suspected to contain *Listeria* bacteria may be contacted with a means according to the present invention with or without subsequent further incubation. Therefore, in various embodiments a step of incubating the sample contacted with a means according to the present invention of the present invention, may follow the step of contacting a sample suspected to contain *Listeria* bacteria with a means according to the present invention. However, in various embodiments, the steps of contacting the sample suspected to contain *Listeria* bacteria with a means according to the present invention and incubating the sample contacted with a means according to the present invention may be performed simultaneously. Accordingly, in various embodiments the step of contacting a sample suspected to contain *Listeria* bacteria with a means according to the present invention may include or comprise the said incubation step.

In various other embodiments, the methods of the present invention may not include a step of contacting a sample suspected to contain *Listeria* bacteria with a means according to the present invention, but may include a step of incubating a sample suspected to contain *Listeria* bacteria with a means according to the present invention only. In such embodiments, the incubation step necessarily comprises contacting the sample suspected to contain *Listeria* bacteria with a means according to the present invention.

Furthermore, the methods of identifying, detecting and/or monitoring *Listeria* according to the present invention, including identifying and detecting *Listeria* contamination and *Listeria* infection, may be performed by means of a solid support. The same applies to methods for the selective purification and/or enrichment of *Listeria* cells and/or components of *Listeria* cells according to the present invention. That is, the TSP provided by the present invention may be bound to a solid support when used in methods and assays according to the present invention. Accordingly, the present invention also provides a solid support having immobilized a protein or polypeptide according to the present invention. The present invention provides the use of such a solid support having immobilized a protein or polypeptide according to the present invention in any method and assay provided by the present invention.

A protein or polypeptide provided by the present invention may be immobilized to the solid support by direct or by indirect means. Here, means for direct and indirect immobilization of proteins and polypeptides to a solid support are well known to the one of ordinary skill in the art. In various embodiments, a protein or polypeptide according to the present invention is immobilized to a solid support by a coupling agent. In the present invention, a coupling agent may be a homobifunctional cross-linker (having the same reactive groups on each end of the cross-linker) or a heterobifunctional cross-linker (having different reactive groups on each end of the cross-linker). There are a number of different reactive groups used in cross-linkers that are targeted towards different functional groups on proteins including carboxyls, amines, sulfhydryls, and hydroxyls. These are known to the person skilled in the art. Cross-linkers are generally selected based on their reactivity, length, and solubility. In various embodiments, monofunctional reagents may be used as coupling agents. It will be understood that the present invention is not limited to the aforementioned specific coupling agents. In the present invention coupling may also be performed using activated solid supports, i.e., solid supports having an activated surface. Means and methods for the activation of the surface of a solid support are known to the one of ordinary skill in the art. Such activation provides for a functionalized solid support for immobilization according to the present invention.

In the present invention, the solid support can be any solid phase used in performing immunoassays, including, but not limited to, membranes, beads, microtiter wells, test tubes, reaction tubes, absorptive pads, and the like. In various embodiments, the solid phase material is a latex bead, a glass fiber, a cellulose strip, or a nitrocellulose membrane. In various embodiments, the solid support is a microtiter plate. In various embodiments, the solid phase material is a magnetic particle (paramagnetic or ferromagnetic), a glass particle, an agarose particle, or a luminex particle. Here, the term "particle" includes the term "bead". Magnetic particles (beads) are preferred because they can easily be separated from the sample by using, for example, magnetic means. In the present invention, magnetic particles (beads) exhibit a diameter allowing the binding of a sufficient amount of *Listeria* cells or cell components per particle. In the present invention magnetic particles preferably exhibit a diameter in the range of about 0.1 µm to about 4 µm, more preferably in the range of about 0.5 µm to about 2 µm, still more preferably in the range of about 0.8 µm to about 1.8 µm, and most preferably in the range of about 1.0 µm.

In various embodiments, the methods provided by the present invention may include a step of separation of the solid support with the *Listeria* cells and/or cell components of *Listeria* cells from the sample after the sample has been incubated with a solid support-bound TSP according to the present invention.

In various embodiments, the TSP of the present invention is bound to the solid support prior to performing the incubation step according to the present invention. Accordingly, after incubating or contacting a sample with an immobilized TSP according to this embodiment of the present invention the complex of solid support, TSP and bound *Listeria* cells and/or *Listeria* cell components may be separated from the sample. Preferably, a washing step follows after separating the said complex from the sample.

In various embodiments, a sample suspected to contain *Listeria* bacterial cells or cell components is first contacted and/or incubated with a TSP of the present invention, and subsequently the complex of TSP and *Listeria* cells and/or *Listeria* cell components is immobilized to a solid surface in accordance with the present invention so as to form a complex of solid support, TSP and bound *Listeria* cells and/or *Listeria* cell components. Accordingly, the *Listeria* cells and/or *Listeria* cell components are bound to the solid support via the TSP of the present invention. Subsequently, the complex of solid support, TSP and bound *Listeria* cells and/or *Listeria* cell components may be separated from the sample. Preferably, a washing step follows after separating the said complex from the sample.

In various embodiments, the methods for identifying, detecting or monitoring *Listeria* according to the present invention comprises the steps of (i) contacting and/or incubating a sample suspected to contain *Listeria* bacterial cells and/or cell components of *Listeria* bacteria with a protein or polypeptide according to the present invention; (ii) contacting and/or incubating the complex obtained in step (i) with a solid support; (iii) separating the complex obtained in step (ii) from the sample; (iv) optionally washing the separated complex of step (iii) with a washing buffer; (v) optionally separating the solid support from the separated complex of step (iii) or the separated and washed complex of step (iv); (vi) optionally detecting binding of *Listeria* bacterial cells and/or *Listeria* cell components to a protein or polypeptide according to the present invention. In the aforementioned method the complex obtained in step (i) comprises protein or polypeptide according to the present invention and *Listeria* cells and/or *Listeria* cell components. Furthermore, in the aforementioned method the complex obtained in step (ii) comprises a protein or polypeptide according to the present invention, *Listeria* cells and/or *Listeria* cell components, and the solid support.

In various embodiments, the methods for identifying, detecting or monitoring *Listeria* according to the present invention comprises the steps of (i) contacting and/or incubating a protein or polypeptide according to the present invention with a solid support; (ii) contacting and/or incubating the complex obtained in step (i) with a sample suspected to contain *Listeria* bacterial cells and/or cell components of *Listeria* bacteria; (iii) separating the complex obtained in step (ii) from the sample; (iv) optionally washing the separated complex of step (iii) with a washing buffer; (v) optionally separating the solid support from the separated complex of step (iii) or the separated and washed complex of step (iv); (vi) optionally detecting binding of *Listeria* bacterial cells and/or *Listeria* cell components to a protein or polypeptide according to the present invention. In the aforementioned method the complex obtained in step (i) comprises a protein or polypeptide according to the present invention and a solid support according to the present invention. Furthermore, in the aforementioned method the complex obtained in step (ii) comprises a protein or polypeptide according to the present invention, the solid support, and *Listeria* cells and/or *Listeria* cell components.

In various embodiments of the present invention the sample suspected to contain *Listeria* bacteria undergoes a pre-treatment prior to being contacted and/or incubated with a protein or polypeptide according to the present invention. Such a pre-treatment may be, for example, enrichment of the *Listeria* bacteria in a sample if necessary in order to obtain a sample suitable for being applied to the methods according to the present invention. Furthermore, a pre-treatment may be, for example, homogenisation of a sample suspected to contain *Listeria* bacteria and/or *Listeria* cell components prior to applying the sample to methods according to the present invention.

In various embodiments, a protein or polypeptide according to the present invention is coupled to low molecular substances, preferably to biotin. A low molecular substance may be chemically introduced into a protein or polypeptide of the present invention or by fusion of a protein or polypeptide of the invention with a polypeptide, in which biotin is introduced in vivo or in vitro using another protein. Such polypeptides are, e.g., biotinylation domains, i.e., regions in naturally occurring polypeptides, which are biotinylated. Such biotinylation domains are exhibited, e.g., by the oxalacetate decarboxylase of *Klebsiella pneumoniae* (U.S. Pat. No. 5,252,466 and EP 0 511 747), the *Salmonella typhimurium* oxalacetate decarboxylase, the *Propionibacterium shermanii* transcarboxylase subunit, the biotin carboxyl carrier protein of *Escherichia coli* acetyl-CoA carboxylase, the *Saccharomyces cerevisiae* pyruvate carboxylase or the *Saccharomyces cerevisiae* acetyl-CoA carboxylase. These biotinylation domains are contemplated for use in the present invention. Such a polypeptide, in which biotin is introduced in vivo or in vitro, may, however, also be the Avi-Tag (see U.S. Pat. No. 5,932,433, U.S. Pat. No. 5,874,239, and U.S. Pat. No. 5,723, 584). The Avi-Tag is also contemplated for use in the present invention. Furthermore, in the present invention instead of biotin the so-called Strep-Tag (Skerra, A. & Schmidt, T. G. M. Biomolecular Engineering 16 (1999), 79-86, U.S. Pat. No. 5,506,121) may be used, which is a short amino acid sequence and binds to streptavidin. Furthermore, the well-known His-Tag may be used in the present invention. It is also possible to combine different tags and in such a way as to use the different binding affinities of the different tags, e.g., Strep-Tag and His-Tag, or biotinylation domain and His-Tag. The biotinylation domains as well as the Avi-Tag, the Strep-Tag as well as the His-Tag are preferably coupled to a protein or polypeptide of the present invention using DNA-recombination technology. Preferably, the fusion protein consists of the biotinylation domain of the oxalacetate decarboxylase from *Klebsiella pneumoniae* or the Avi-Tag, the Strep-Tag or the His-Tag, which are bound to the N-terminal end of a protein or polypeptide of the invention at their C-terminal end.

The person skilled in the art is generally well aware of techniques for manipulating proteins for use in detection procedures, and such techniques may be applied in the methods and assays of the present invention. That is, in the present invention these techniques are used for chemically modifying the TSP used in the methods and assays of the present invention in order to provide mean for signalling in the detection procedures of the present invention. Thus, chemical modifications of TSPs of the present invention include, but are not limited to, the use of dyes, enzymes and biotin.

It is contemplated that any such techniques may be applied to the methods and assays of the present invention.

The TSP of the present invention may be adapted by a targeted or random mutagenesis in its host specificity and its binding behaviour, respectively, to the solid support structures described herein. By means of mutagenesis, mutations may be introduced which may be amino acid additions, deletions, substitutions, or chemical modifications. These mutations may produce an alteration of the amino acid sequence in the binding region of the TSP, with the intention to adapt the specificity and binding affinity to the experimental requirements.

Samples

In various embodiments, the sample according to the present invention is a clinical sample, preferably a clinical sample obtained from a patient. In various embodiments the patient is a patient suffering from a *Listeria* infection. In various embodiments the patient is a patient suspected of suffering from a *Listeria* infection.

In various embodiments, the sample is a biological sample. A biological sample according to the present invention includes, but is not limited to, a blood sample, serum, sputum, faeces, urine, a lung biopsy, and saliva.

In various embodiments, the sample is an environmental sample.

In various embodiments, the sample according to the present invention is an alimentary sample. Preferably, the alimentary sample is obtained from a food or feed product or a food or feed precursor. A food or feed precursor is a precursor that is subjected to or used in the preparation of a food or feed product. In various embodiments, the alimentary sample according to the present invention is a sample from a food or feed product, or from a food or feed precursor to be used for human consumption. More preferably, the alimentary sample according to the present invention is from egg, meat, seafood, milk, sauce or salad dressing. In various embodiments, the sample is from a dairy product. As used herein, the term "dairy product" is intended to include any food product made using milk or milk products, including, but not limited to, milk, yoghurt, ice cream, cheese, butter, and cream. In various embodiments, the sample is a water sample suspected to contain *Listeria* bacteria.

As used herein, a sample according to the present invention is a sample suspected to contain *Listeria*. Here, *Listeria* comprises *Listeria* bacteria as described herein elsewhere.

Of course, in the present invention a sample may comprise microorganisms other than *Listeria*, wherein such other microorganisms also include pathogenic microorganisms other than pathogenic *Listeria*.

Kits

The present invention provides a kit comprising a nucleic acid molecule of the present invention, a vector of the present invention, a host cell of the present invention, a protein of the present invention including a chimeric protein of the present invention. The present invention also provides a kit comprising a composition or solution of the present invention. In various embodiments, the kit according to the present invention is a kit for use in a method for identifying *Listeria* according to the present invention, or a kit for carrying out a method for identifying *Listeria* according to the present invention. In various embodiments, the kit according to the present invention is a kit for use in a method for detecting *Listeria* according to the present invention, or a kit for carrying out a method for detecting *Listeria* according to the present invention. In various embodiments, the kit according to the present invention is a kit for use in a method for monitoring *Listeria* according to the present invention, or a kit for carrying out a method for monitoring *Listeria* according to the present invention. In various embodiments, the kit according to the present invention is a kit for use in a diagnostic method according to the present invention, or a kit for carrying out a diagnostic method according to the present invention. In various other embodiments, the kit according to the present invention is a kit for cleaning *Listeria* contamination according to the present invention.

Further Definitions

In the present invention, "Percentage (%) of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity", in the context of two or more nucleic acids or polypeptide sequences, refer to two or more sequences or sub-sequences that are the same or have a specified percentage of amino acid resides or nucleotides that are the same, when compared and aligned for maximum correspondence over a comparison window, or designated region as measured using one of the following sequence comparison algorithms or by manual alignment and visual inspection. Such sequences are then said to be "substantially identical". This definition also refers to the complement of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based an the program parameters.

The terms nucleic acid molecule and nucleic acid sequence may be used herein interchangeably.

As discussed herein there are numerous variants of the proteins and polypeptides of the present invention. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Deletions are characterized by the removal of one or more amino acid residues from the protein sequence. Typically, no more than about from 2 to 6 residues are deleted at any one site within protein molecules according to the present invention. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known to the ones skilled in the art. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one amino acid residue has been removed and a different amino acid residue inserted in its place such that a conservative substitution is obtained. The meaning of a conservative substitution is well known to the person skilled in the art.

Certain post-translational modifications are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the C-terminal carboxyl. Such post-translational modifications are also contemplated by the present invention.

The term "JS-tag" as used herein relates to a polypeptide, which comprises a sequence as shown in SEQ ID NO: 1 of international patent application WO 2008/077397 (PCT/EP2007/002320) as well as derivatives thereof. In various embodiments of the present invention the JS-tag is selected from the JS-tags as referred to in WO 2008/077397. In various embodiments of the present invention, the JS-tag comprises the sequence of SEQ ID NO: 1 of WO 2008/077397. In various other embodiments of the present invention, the JS-tag comprises a sequence of any one of SEQ ID NOs: 2-18 of WO 2008/077397. The sequences of SEQ ID NOs: 1-18 of WO 2008/077397 show the alpha-subunit of the oxalacetate decarboxylase of *Klebsiella pneumoniae* and variants thereof (see also U.S. Pat. No. 5,252,466 and EP 0 511 747). This alpha-subunit represents a biotinylation domain, i.e. a region present in naturally occurring polypeptides, which are biotinlyated.

The methods of the present invention may be used with any detection strategy, including, but not limited to, probe hybridization, lateral flow assays, PCR, ELISA, ELFA (enzyme-linked fluorescent assay), enzymatic detection, plasmon resonance technique, magnetic bead-based methods and the like. Detection strategies based on using chromogenic media to detect *Listeria* genus-specific beta-glucosidase activity are also contemplated by the present invention. Moreover, in the present invention other techniques based on chromogenic media can be used to distinguish between *Listeria monocytogenes* and *Listeria ivanovii* from other *Listeria* species by assaying phosphatidylinositol phospholipase C (PI-PLC) activity. It has been shown that certain species of the genus *Listeria* (such as *Listeria monocytogenes* and *Listeria ivanovii*) secrete PI-PLC into the culture medium (Leimeister-Wachter et al., Mol. Microbiol. (1991) 5(2), pp. 361-366; J. Mengaud et al., Mol. Microbiol. (1991) 5(2), pp. 367-372; and Goldfine et al., Infection and Immunity (1992) 60(10), pp. 4059-4067). Assaying a sample for the presence of *Listeria monocytogenes* according to the present invention also includes exposing the sample after incubation with means according to the present invention to an aptamer that specifically binds one of the following proteins: *Listeria monocytogenes* internalin A protein, *Listeria monocytogenes* internalin E protein, and *Listeria monocytogenes* 0610 protein (cf. U.S. Pat. No. 7,645,582 B2). The presence of *Listeria monocytogenes* in the sample is detected when the aptamer binds the protein present in the sample. The detection of *Listeria* according to the present invention is generally performed by direct and/or indirect detection of *Listeria* cells or cell wall components. By direct methods, *Listeria* cells or cell wall components are detected. In the present invention, indirect methods used for *Listeria* detection include, but are not limited to, antibody assays such as antibody-ELISA, haemagglutination inhibition, complement fixation, and the recently appearing novel methods such as biosensors, bioluminometry, fluorescence polarisation, and chemoluminescence.

The term "*Listeria*" as used herein means the bacterial genus *Listeria*. In the present invention, the genus *Listeria* encompasses all known *Listeria* species. In particular, in the present invention the genus *Listeria* includes, but is not limited to, the following *Listeria* species: *L. monocytogenes, L. seeligeri, L. ivanovii, L. innocua, L. welshimeri, L. grayi* ssp. *grayi*, and *L. grayi* ssp. *murrayi*.

In the present invention, the preferred *Listeria* species is a *Listeria* species that is pathogenic to human beings and/or animals.

In various embodiments of the present invention, the preferred *Listeria* species is *Listeria monocytogenes*, which is pathogen to both human and animals. This applies in particular to the therapeutic and non-therapeutic methods of the present invention.

In the present invention *Listeria monocytogenes* includes serotypes 1/2a, 1/2b, 1/2c, 3a, 3b, 3c, 4a, 4ab, 4b, 4c, 4d, 4e, and 7. In various embodiments, the *Listeria* species is selected from the group consisting of *L. monocytogenes* serotype 1/2a, *L. monocytogenes* serotype 1/2b, *L. monocytogenes* serotype 1/2c, *L. monocytogenes* serotype 3a, *L. monocytogenes* serotype 3b, *L. monocytogenes* serotype 3c, *L. monocytogenes* serotype 4a, *L. monocytogenes* serotype 4ab, *L. monocytogenes* serotype 4b, *L. monocytogenes* serotype 4c, *L. monocytogenes* serotype 4d, *L. monocytogenes* serotype 4e, and *L. monocytogenes* serotype 7.

In more preferred embodiments of the present invention the *Listeria* species is selected from the group consisting of *L. monocytogenes* 1142 serovar 1/2a, *L. monocytogenes* 1042 serovar 4b, *L. monocytogenes* 1019 serovar 4c, *L. monocytogenes* 1001 serovar 1/2c, *L. monocytogenes* EGDe serovar 1/2a, *L. monocytogenes* SLCC 7150 serovar 1/2a, *L. monocytogenes* SLCC 7154 serovar 1/2c, *L. monocytogenes* SLCC 7290 serovar 1/2c, *L. monocytogenes* 0756062 serovar 1/2c, *L. monocytogenes* WSLC1485 serovar 1/3a, *L. monocytogenes* WSLC 11082 serovar 1/3c, *L. monocytogenes* WSLC 11083 serovar 1/3c, *L. monocytogenes* ScottA serovar 4b, *L. monocytogenes* WSLC 1048 serovar 4d, *L. monocytogenes* 8309032 serovar 4d, and *L. monocytogenes* 8309033 serovar 4e.

In various embodiments, the preferred *Listeria* species is *Listeria ivanovii*, which is pathogenic to animals. In preferred embodiments, the *Listeria* species is *Listeria ivanovii* serotype 5.

The literature discloses reports about diseases in human beings resulting from infection with *Listeria* seeligeri (Rocourt et al. 1987) and *L. ivanovii* (Cummins et al. 1994). In the present invention *Listeria* seeligeri includes serotypes I/2a, I/2b, I/2c, 4b, 4c, 4d, and 6b. In various embodiments, the *Listeria* species is selected from the group consisting of *L. seeligeri* serotype I/2a, serotype I/2b, serotype I/2c, serotype 4b, serotype 4c, serotype 4d, and serotype 6b.

In the present invention *Listeria* innocua includes serotypes 3, 6a, 6b, 4ab, and U/S. In various embodiments, the *Listeria* species is selected from the group consisting of *L. innocua* serotype 3, *L. innocua* serotype 6a, *L. innocua* serotype 6b, *L. innocua* serotype 4ab, and *L. innocua* serotype U/S. Preferably, *L. innocua* is *L. innocua* 2011 serotype 6a.

In the present invention *Listeria* welshimeri includes serotypes I/2a, 4c, 6a, 6b, and U/S. In various embodiments, the *Listeria* species is selected from the group consisting of *L. welshimeri* serotype I/2a, *L. welshimeri* serotype 4c, *L. welshimeri* serotype 6a, *L. welshimeri* serotype 6b, and *L. welshimeri* serotype U/S.

In the present invention *Listeria grayi* includes serotype Grayi. In various embodiments, the *Listeria* species is *L. grayi* serotype Grayi.

The term "CBD", i.e. cell wall binding domain, as used herein, relates to polypeptide fragments, wherein the respective amino acid sequence corresponds to a portion (or domain) in endolysins. Said portion/domain is responsible for binding of endolysins to the *Listeria* cell wall. Said polypeptide fragments are not (or not substantially) enzymatically active. The term "domain" or "protein domain", as used herein, denotes a portion of an amino acid sequence that either has a specific functional and/or structural property. On the basis of amino acid sequence homologies, domains can frequently be predicted by employing appropriate computer programs that compare the amino acid sequences in freely available databases with known domains, e.g., Conserved Domain Database (CDD) at the NCBI (Marchler-Bauer et al., 2005, Nucleic Acids Res. 33, D192-6), Pfam (Finn et al., 2006, Nucleic Acids Research 34, D247-D251), or SMART (Schultz et al., 1998, Proc. Natl. Acad. Sci. USA 95, 5857-5864, Letunic et al., 2006, Nucleic Acids Res 34, D257-D260).

Whenever reference is made to the specificity or activity of the polypeptide of SEQ ID NO: 2 (P825Orf2), the binding specificity of P825Orf2 to *Listeria* cells is meant. In the present invention, binding specificity of P825Orf2 to *Listeria* cells means binding specificity to the cell wall of *Listeria* bacteria, preferably to bacteriophage receptors on *Listeria* cells. Specifically, bacteriophage receptors on *Listeria* cells include, but are not limited to, teichoic acids.

The terms "protein" and "polypeptide" are used in the present invention interchangeably. Furthermore, the term "sv" represent the well known abbreviation of the term "serovar".

The term "dye" or "dye label" as used herein refers to a compound that emits light to produce an observable detectable signal.

The term "label" or "labelled", as used herein, refers to a chemical moiety or protein that is directly or indirectly detectable (e.g., due to its spectral properties, conformation or activity) when attached to a protein, polypeptide, target or compound as described herein, and when used in the present methods, also including reporter molecules, solid supports and carrier molecules. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate.

When particular embodiments of the invention are described herein, the corresponding paragraphs/text passages of the description invariably make reference to means and/or methods described elsewhere in the description. In this context, terms like "according to the present invention", "of the present invention" and "provided by the present invention" are used. That is, when a particular embodiment of the invention is described in a certain paragraph or text passage, reference is made to means and/or methods "according to the present invention" or "of the present invention", which are described elsewhere in the description. For a particular embodiment described, such references are intended to incorporate for the particular embodiment all means and/or methods, which are described elsewhere in the description and which are provided by the present invention and therefore form part of the scope of the invention. For example, if the description of a particular embodiment refers to "the TSP according to the present invention" or "the TSP of the present invention", or "the TSP provided by the present invention", it is intended that all TSPs, which are described elsewhere in the description, and which are provided by the present invention and therefore form part of the scope of the invention, are applicable to the particular embodiment. This particularly applies, for example, to fragments and variants of polypeptides according to the present invention, which are defined in the present invention and which are applicable to the various embodiments described throughout the application text.

The above principle applies to all embodiments making use of terms like "according to the present invention", "of the present invention" and "provided by the present invention". It goes without saying that not each embodiment described herein can specifically mention the means and/or methods of the invention, which are already defined elsewhere in the description, and which are applicable to the various embodiments described throughout the application text. Otherwise, each patent application would comprise several hundreds of description pages.

Furthermore, terms like "in various embodiments" and "in various other/further embodiments" mean "in various embodiments of the present invention" and "in various other/further embodiments of the present invention"

The invention is exemplified by the examples, which are not considered to limit the scope of the present invention.

EXAMPLES

Example 1

Cloning of HisJS-P825Orf2

Genomic DNA of bacteriophage P825 was isolated according to Lambda kit, Qiagen, Hilden, Germany, and used as template for cloning HisJS-P825Orf2. The following primers were used for amplifying P825Orf2:
Forward primer: cgtta ggatcc ATGACTAACTATAT-CATGGCAAA (ggatcc=BamH1 restriction enzyme site) (SEQ ID NO:3).
Reverse primer: ggtagc gtcgac TTAGTCAATATAAAAT-TCTATTGGCG (gtcgac=Sal1 restriction enzyme site) (SEQ ID NO:4).

After restriction with restriction enzymes BamH1 and Sal1 P825Orf2 was cloned into pQE30-HisJS vector (pQE30 is a commercially available vector, Qiagen, Hilden, Germany). The cloning was controlled by expression of HisJS-P825Orf2 and sequencing of the insert of the recombinant vector pQE30-HisJS-P825Orf2.

His-JSP825Orf2 describes the nucleotide and amino acid sequence of the novel *Listeria* bacteriophage tailspike protein P825Orf2 N-terminally fused to hexa-histidine tag and a JS-tag, wherein the JS-tag is the α-subunit of the oxalacetate decarboxylase of *Klebsiella pneumoniae* as described in WO 2008/077397.

Example 2

Purification of HisJS-P825Orf2 Tailspike Protein

Purification of HisJS-P825Orf2 tailspike protein was performed as follows:
In vivo biotinylated HisJS-P825Orf2 was expressed in large scale (2 l LB-medium, incubation at room temperature (RT) under shaking until an optical density ($OD_{600}$) of about 0.6 was reached). Protein expression was induced with 1 mM IPTG and 20 ml biotin solution (5 mM Biotin, 50 mM Tris-HCl, 100 mM NaCl, 2 mM EDTA, pH 8). Incubation was performed at RT overnight under shaking, and cells were harvested the next day by centrifugation. For cell lysis cells were re-suspended in 40 ml buffer A (20 mM Tris-HCl, 500 mM NaCl, 20 mM Imidazol, pH 7.5). Subsequently, 1 mg/ml Lysozyme, 1 mg/ml DNAse I and 1 mM $MgCl_2$ were added to the cell suspension, which was then incubated for 30 min at RT. Upon sonication cells were pelleted by centrifugation (SS-34 rotor, 20 min, 13,000 rpm, 4° C.).

Affinity purification of soluble expressed in vivo biotinylated HisJS-P825Orf2 was performed using two HisTrapFF crude columns (GE Healthcare, 1 ml). Specifically, the supernatant of lysed cells was loaded to two HisTrapFF crude columns with Âkta purifier (1 ml/min). The columns were washed with buffer A until the $UV_{280}$ signal reached 10 mAU. Protein was eluted over a gradient with 20 column volumes from 0% to 100% buffer B (25 mM Tris-HCl, 500 mM NaCl, 500 mM Imidazol, pH 7.5). All fractions were analysed via SDS-PAGE. The elution fractions containing HisJS-P825Orf2 were pooled and dialysed two times against 2 l dialysis buffer (20 mM Tris-HCl, 50 mM NaCl, 2 mM EDTA, pH 8) overnight and for 3 h. The dialysed protein was filtered under sterile conditions, and the concentration of the protein was determined by UV-spectrometry at $UV_{280}$ and the extinction coefficient.

Example 3

Propagation of Phage P825

The phage host ProCC S1138 was inoculated in 1 ml TB-media (Merck, Inc.) and incubated for 5 h at 37° C. and 900 rpm in an "Eppendorf shaker" until clouds of bacteria became visible. 250 µl of the culture were inoculated in 10 ml TB-medium with ions (TB-media, 2 mM $CaCl_2$, 10 mM $MgSO_4$) and incubated at RT for 4 h under shaking. 1 µl P825 phage was added to the culture and the culture was incubated overnight at RT. The next day bacteria were centrifuged down for 10 min and 4,500 rpm. The supernatant with phage was filtered with a 0.2 µm filter to remove residual bacteria and residual pieces of bacteria. In order to determine the phage concentration in the lysate, 5 µl of 0, $10^{-1}$, $10^{-2}$, $10^{-3}$, $10^{-4}$, $10^{-5}$, $10^{-6}$ and $10^{-7}$ dilutions were dropped on a TB-Top-Agar plate containing the phage host and incubated at 37° C. over night. The next day single plaques of one dilution were counted (>5). Multiplication with both dilution factors revealed the pfu/ml (pfu=plaque forming unit). For example, 25 single plaques on the $10^{-6}$ dilution revealed $5 \times 10^9$ pfu/ml ($25 \times 200 \times 10^6$).

Example 4

Phage Lysis

For phage lysis 250 µl overnight cultures of *Listeria* strains were added to 3 ml TB-top-agar (TB-media, 0.75% (w/v) Agar, 2 mM $CaCl_2$, 10 mM $MgSO_4$) and poured into a TB-agar plate. 5 µl of *Listeria* phage P825 ($10^9$ pfu/ml) were spotted onto the top-agar plate and dried for about 30 min. The plate was incubated overnight at RT. Evaluation of the lysis spots was done in accordance with the following:
no spot: indicated by "−"
turbid spot: indicated by "(+)"
a clear lysis spot: indicated by "+"
The results are shown in Table 1 of the present application.

Example 5

Inclusivity Testing with In Vivo Biotinylated *Listeria* Phage Tailspike Protein HisJS-P825Orf2

In order to test the binding spectrum of in vivo biotinylated tailspike protein, various *Listeria* strains of various serogroups (1/2, 3, 4, 5 and 6) were tested in Cell-ELISA. Strains that show a high unspecific binding to StrepTactin-HRP conjugate or show weak "(+)" binding ("(+)") in Cell-ELISA were tested again in Beadsbinding-Test. Results of the inclusivity testing were compared to phage lysis spectra in order to show a consensus between binding of the tailspike protein P825Orf2 and phage lysis.

Cell-ELISA:
  Listeria cells of different Serovars belonging to serogroups 1/2, 3, 4, 5, 6 were diluted ⅕ from an overnight culture in TB media and cultivated up to an $OD_{600}$ of 1.
  Cells were washed twice with PBS buffer pH 8.
  100 µl cell suspension per well were coated to a maxiSorp microtiter plate for 1 h at RT under shaking (Eppendorf shaker, 600 rpm).
  wells were washed once with 200 µl washing buffer (10 mM Tris-HCl, 171 mM NaCl, 0.1% Tween 20; pH 7.2).
  MaxiSorp surface was blocked with 200 µl blocking buffer (washing buffer, 0.5 c/0 (w/v) BSA) for 1 h at RT or overnight at 4° C.
  wells were washed once with 200 µl washing buffer.
  In vivo biotinylated bacteriophage tailspike protein was diluted in blocking buffer to a concentration of 5 µg/ml.
  100 µl protein suspension per well were incubated for 30 min at RT under shaking (Eppendorf shaker, 600 rpm).
  wells were washed three times with 200 µl washing buffer.
  bound protein was detected with StrepTactin-HRP (HRP=horse raddish peroxidase; IBA) conjugate, diluted 1:5000 in blocking buffer. 100 µl per well and incubation for 30 min at RT under shaking (Eppendorf shaker, 600 rpm).
  wells were washed four times with 200 µl washing buffer.
  StrepTactin-HRP conjugate that bound on the tailspike protein on the Listeria cells was detected with a colorimetric substrate (ABTS). 100 µl ABTS buffer per well; absorption at 405 nm against 620 nm was measured after 60 min staining against uncoated wells.
  The signal of every strain was divided through the signal without cells and the signal without protein was subtracted from this ratio. Now this value is standardized to the value from Listeria monocytogenes strain Sv 4b (ProCC S776) that is tested as positive control at each microtiterplate ((value new strain/value S776)×100). Values over 70 are listed in Table 1 with a "+", values between 10-70 are listed with "(+)" and values smaller than 10 are listed with a "–".

Beadsbinding Test:
  Listeria cells of different Serovars belonging to serogroups 1/2, 3, 4, 5, 6 were diluted ⅕ from an overnight culture in TB media and cultivated up to an $OD_{600}$ of 1.
  Cells were diluted to a concentration of $10^4$ cfu/ml in PBST buffer (2.25 mM $NaH_2PO_4$, 7.75 mM $Na_2HPO_4$, 150 mM NaCl, pH 8.0).
  In a sample volume of 500 µl, in vivo biotinylated bacteriophage tailspike protein (HisJS-P825Orf2) was added to a concentration of 5 µg/ml, mixed for 10 s, and MCB PVB3 magnetic particle (Streptavidin coated magnetic particle, Microcoat GmbH, Bernried, Germany) were added in a concentration of 200 µg/ml.
  Bacteriophage tailspike protein, Listeria cells and magnetic particle were incubated in an overhead rollator for 20 min at room temperature.
  Magnetic particle-tailspike-Listeria cell complexes were collected by magnetic separation. Supernatant was collected in a separate tube.
  1 ml of PBST was added and samples were incubated rollating for 10 minutes at RT
  Magnetic particle-tailspike-Listeria cell complexes were collected by magnetic separation. Supernatant was pooled with supernatant from first step.
  Beads were re-suspended in 500 µl PBST.
  Beads and Supernatant were onto TB-agar (TB-media, 1.5% (w/v) agar) and incubated over night at 37° C.
  On the next day the colonies were counted. Captured cells are determined in comparison to cells present in the supernatant. Cells bound unspecific to the streptavidin-coated magnetic particle are determined from controls without addition of bacteriophage tailspike protein. Unspecific binding is observed in a range of up to 1.5%.

TABLE 1

Comparison of HisJS-P825Orf2 tailspike binding specificity with host specificity of Phage P825. ProCC s relates to an internal culture collection.

| Listeria species | serovar | ProCC S | Binding: HisJS-P825Orf2 | Lysis: Phage P825 |
|---|---|---|---|---|
| monocytogenes | 1/2a | 679 | + | + |
| monocytogenes | 1/2a | 992 | + | (+) |
| monocytogenes | 1/2a | 1095 | + | + |
| monocytogenes | 1/2b | 996 | + | (+) |
| monocytogenes | 1/2b | 997 | + | – |
| seeligeri | 1/2b | 1153 | + | + |
| welshimeri | 1/2b | 1158 | + | + |
| monocytogenes | 1/2c | 1002 | + | + |
| monocytogenes | 1/2c | 1003 | + | + |
| monocytogenes | 1/2c | 2867 | + | + |
| monocytogenes | 3a | 1135 | + | + |
| monocytogenes | 3a | 1576 | + | + |
| monocytogenes | 3a | 2966 | + | + |
| monocytogenes | 3a | 2967 | – | – |
| monocytogenes | 3a | 2968 | + | + |
| monocytogenes | 3a | 2969 | + | (+) |
| monocytogenes | 3a | 2970 | + | (+) |
| monocytogenes | 3a | 2971 | + | + |
| monocytogenes | 3b | 1136 | + | +/+ |
| monocytogenes | 3b | 1137 | + | +/+ |
| monocytogenes | 3b | 2972 | + | + |
| monocytogenes | 3b | 2973 | + | + |
| monocytogenes | 3b | 3024 | + | – |
| seeligeri | 3b | 1154 | + | + |
| seeligeri | 3b | 2978 | + | + |
| seeligeri | 3b | 2979 | + | (+) |
| seeligeri | 3b | 2980 | (+) | (+) |
| seeligeri | 3b | 2981 | + | + |
| seeligeri | 3b | 2982 | + | + |
| seeligeri | 3b | 2983 | + | + |
| seeligeri | 3b | 2984 | + | + |
| seeligeri | 3b | 2985 | + | + |
| seeligeri | 3b | 2986 | + | (+) |
| seeligeri | 3b | 2987 | + | (+) |
| seeligeri | 3b | 2988 | + | + |
| seeligeri | 3b | 2989 | + | + |
| seeligeri | 3b | 2990 | + | (+) |
| seeligeri | 3b | 2991 | (+) | + |
| seeligeri | 3b | 3026 | + | + |
| monocytogenes | 3c | 1138 | + | + |
| monocytogenes | 3c | 1139 | + | + |
| monocytogenes | 3c | 2974 | + | + |
| monocytogenes | 3c | 2975 | – | – |
| monocytogenes | 3c | 2976 | + | + |
| monocytogenes | 3c | 2977 | + | + |
| monocytogenes | 4a | 1141 | (+) | + |
| monocytogenes | 4b | 776 | + | + |
| monocytogenes | 4b | 1004 | + | + |
| monocytogenes | 4b | 1006 | + | + |
| monocytogenes | 4b | 1007 | + | + |
| monocytogenes | 4c | 1142 | + | + |
| monocytogenes | 4d | 1144 | + | + |
| monocytogenes | 4d | 2919 | + | + |
| monocytogenes | 4e | 2920 | + | + |
| monocytogenes | 4e | 1145 | + | + |
| monocytogenes | 4b | 1005 | + | + |

TABLE 1-continued

Comparison of HisJS-P825Orf2 tailspike binding specificity with host specificity of Phage P825. ProCC s relates to an internal culture collection.

| Listeria species | serovar | ProCC S | Binding: HisJS-P825Orf2 | Lysis: Phage P825 |
|---|---|---|---|---|
| ivanovii | 5 | 857 | + | + |
| ivanovii | 5 | 1012 | + | + |
| ivanovii | 5 | 1014 | + | + |
| ivanovii | 5 | 1015 | + | + |
| ivanovii ssp. Iondoniensis | 5 | 1164 | + | + |
| ivanovii ssp. Ivanovii | 5 | 1150 | + | + |
| innocua | 6a | 1147 | + | (+) |
| innocua | 6b | 773 | + | + |
| welshimeri | 6b | 1575 | + | + |

Example 6

Exclusivity Testing with In Vivo Biotinylated *Listeria* Phage Tailspike Protein HisJS-P825Orf2 Compared with the Cell Wall Binding Domain of Ply511

Streptavidin-coated microtiter plates were coated with 1 μg/ml in vivo biotinylated JS-CBD511 and HisJS-P825Orf2, respectively, in washing buffer with 0.5% (w/v) BSA (10 mM Tris-HCl, 171 mM NaCl, 0.1% Tween 20; pH 7.2) for 1 h at RT. After three washing steps with 200 μl washing buffer per well, different non-*Listeria* strains that are known to cross react with CBD511 were incubated on the microtiterplate. 100 μl per well were incubated for 1 h at RT with $10^6$-$10^9$ cfu/ml. Wells were washed three times with 200 μl washing buffer. 100 μl in vivo biotinylated JS-CBD511 (0.2 μg/ml) mixed with StrepTactin-HRP conjugate (1:5000) in washing buffer with 0.5 (w/v) BSA were incubated for 1 h on each strain. Wells were washed three times with 200 μl washing buffer, and bound conjugate was detected with ABTS solution. The colorimetric reaction was measured after 60 min at 405/600 nm. The results are shown in FIG. 1.

Example 7

Affinity Testing of In Vivo Biotinylated *Listeria* Phage Tailspike Protein HisJS-P825Orf2

Affinity testing of in vivo biotinylated *Listeria* phage tailspike protein HisJS-P825O112 was performed using the Beadsbinding test (see Example 5). Here protein concentrations from 0.001 μg/ml to 1 μg/ml were used in the test. In order to control unspecific binding one test without protein was included. The results are shown in FIG. 2.

REFERENCES

McLauchlin J. (1987). *Listeria monocytogenes*, recent advances in the taxonomy and epidemiology of listeriosis in humans. Journal of Applied Bacteriology 63(1):1-11.

Oevermann A., Botteron C., Seuberlich T. et al. (2008). Neuropathological survey of fallen stock: active surveillance reveals high prevalence of encephalitic listeriosis in small ruminants. Veterinary Microbiology 130 (3-4):320-329.

Gillespie I. A., McLauchlin J., Grant K. A. et al. (2006). Changing pattern of human listeriosis, England and Wales, 2001-2004, Emerging Infectious Diseases 12(9):1361-1366.

Goulet V., Hedberg C., Le Monnier A., and de Valk H. (2008). Increasing incidence of listeriosis in France and other European countries, Emerging Infectious Diseases 14(5): 734-740.

Gillespie I. A., McLauchlin J., Little C. L. et al. (2009). Disease presentation in relation to infection foci for non-pregnancy associated human listeriosis in England and Wales, 2001 to 2007. J. Clinic. Microbiology 47(10):3301-3307.

Rocourt J, Schrettenbrunner A, Hof H, Espaze EP, 1987. New species of the genus *Listeria: Listeria seeligeri*. *Pathol Biol (Paris)* September: 35(7):1075-80. [Article in French]

Cummins A J, Fielding A K, McLauchlin J. 1994. *Listeria ivanovii* infection in a patient with AIDS. J Infect. 1994 January: 28(1):89-91.

Doumith, M., Cazalet C., Simoes N., et al. (2004). New aspects regarding evolution and virulence of *Listeria monocytogenes* revealed by comparative genomics and DNA arrays, Infection and Immunity 72(2):1072-1083.

Oevermann A., Zurbriggen A., and Vandevelde M. (2010). Rhombencephalitis caused by *Listeria monocytogenes* in humans and ruminants: A zoonosis on the rise?. Interdisciplinary Perspectives on Infectious Diseases, Volume 2010, Article ID 632513, 22 pages.

Hagens S. and Loessner M. J. (2007). Application of bacteriophages for detection and control of foodborne pathogens, Appl. Microbiol. Biotechnol. 76(3):513-519.

SEQUENCE LISTING

SEQ ID NO: 1: Nucleotide sequence of tailspike protein P825Orf2 (1,896 nucleotides; origin: *Listeria* bacteriophage ProCC P825)

```
  1  atgactaact atatcatggc aaactcctac
     gcctttgacg gcacggatga ttttattcat 61  ggcgtttacg aggtagacga aacattaact
     actgttaaga tattacttaa cggaactgat 121  actaacttaa atgcaattgc aggattcact
     aatgggacaa cctttatggc tgacgtttcc 181  actatcaaat ctcaaatcac attaaccaca
     gtggttacaa tgattatgta taatggaact 241  aaagagcttg cgagatgtcc tgttcctatc
     tatagccaag ctaatccacc agttccaaaa 301  tcagctgaca agaaatacac tctagcattg
     gacttagtta aagatactga aaacgtggta 361  ctaatatccc gcattgctga caaagattta
     acatccgtat tagttaagct aaccaacaac 421  ggagaagcaa taaacttagt gggacgtacc
     ccgctatttg agtgtcaatt acccgcacaa 481  acaggtgagt atgctaactt cgtccgtgat
     gatgggatag caaatggcaa tatgattatt 541  gtagatgccg aacaaggaat cattcaatac
     aactttgtta aagagacttt ctccaaagta 601  ggggctatta acattgccta ttttgctttta
     gaaacaccag ttggtgatat tgtaaaacgt 661  gtcacaactc gtaactttaa aatcattgta
     acagatagtg ctattgaagg aaagataaat 721  gctgacgatt acatctctga cattgagtcg
     cttaaagctg agattgaaat taggcttgct
```

SEQUENCE LISTING

```
 781 cctgtaattg ctgaaatggt tcaactgaaa
     gcagatgtgg cagatgctag tgcacagatg 841 gatgagatag aagcactgat tacagctaac
     caagtaatca aaacagctga tgcagttaac 901 tggcagaaac agaagattac tgatgacaca
     ggtgccaact tacttacaac tggctcagac 961 acttcaaaag atattcttga tattataaaa
     acagcaggaa taggtttacg aacattctat 1021 gcagtatcag gtgctgtaaa taacccaacg
     gctaatactc ctttaagagg aatttctcat 1081 ctaacaacag ctacaaccgg atgggtaatt
     ggatgggatt cctttggaaa ctcttattca 1141 actttcttaa atggaacagc tggttgggta
     cttccttgga agagaacgc cacaatgtct 1201 gatgttgcta accaattagc aaccgcagtt
     tctacttaa acactagaat ggattccatg 1261 cagaacatcc agctatttga taatagcggt
     gttcctatag taaatctaga tacggacagt 1321 ggattagata tttacacaga gctaaataaa
     gttccggctg gtatgtatat gacacgaatt 1381 tctggtactg ctggaacaac aaatcctaat
     actaatgttc ctcctaccac catccgggga 1441 tatacctata ttgaggtaca aggtacttgg
     gggaatttat atggagtagg ctccaaccag 1501 actatggtaa tgaaccaact aaatagcgga
     gtgtggcgag atggagagt gcaagatgca 1561 cgagatactg ctggataaa tatcacagga
     tttaattctg gatggtcaac tgatgctaca 1621 aaccctccgg catatcgtaa agtaggtaat
     aaggtttcat tacgtggagt tgttcacatg 1681 gataccgctg ctaagaaagg tgttatcgca
     acacttcctg ctggttatcg tccaatggta
```

```
1741 ggtaatcaaa atggttggat atgtgcacgt
     caaaccactg gtgttaactt tatggcagag 1801 gtttatgtaa gcagtgcagg taacttagag
     gttgtatgga taaatggtaa cggaacacaa 1861 ggtatttggt taacgccaat agaatttat attgac
```

SEQ ID NO: 2: Amino acid sequence of tailspike protein P825Orf2 (632 amino acid residues; origin: *Listeria* bacteriophage ProCC P825)

```
  1 MTNYIMANSY AFDGTDDFIH GVYEVDETLT
    TVKILLNGTD TNLNAIAGFT

51 NGTTFMADVS TIKSQITLTT VVTMIMYNGT
    KELARCPVPI YSQANPPVPK

101 SADKKYTLAL DLVKDTENVV LISRIADKDL
    TSVLVKLTNN GEAINLVGRT

151 PLFECQLPAQ TGEYANFVRD DGIANGNMII
    VDAEQGIIQY NFVKETFSKV

201 GAINIAYFAL ETPVGDIVKR VTTRNFKIIV
    TDSAIEGKIN ADDYISDIES

251 LKAEIEIRLA PVIAEMVQLK ADVADASAQM
    DEIEALITAN QVIKTADAVN

301 WQKQKITDDT GANLLTTGSD TSKDILDIIK
    TAGIGLRTFY AVSGAVNNPT

351 ANTPLRGISH LTTATTGWVI GWDSFGNSYS
    TFLNGTAGWV LPWKENATMS

401 DVANQLATAV STLNTRMDSM QNIQLFDNSG
    VPIVNLDTDS GLDIYTELNK

451 VPAGMYMTRI SGTAGTTNPN TNVPPTTIRG
    YTYIEVQGTW GNLYGVGSNQ

501 TMVMNQLNSG VWRGWRVQDA RDTGWINITG
    FNSGWSTDAT NPPAYRKVGN

551 KVSLRGVVHM DTAAKKGVIA TLPAGYRPMV
    GNQNGWICAR QTTGVNFMAE

601 VYVSSAGNLE VVWINGNGTQ GIWLTPIEFY ID
```

The invention claimed is:

1. An isolated chimeric polypeptide comprising a P825Orf2 amino acid sequence at least 75% identical to the amino acid sequence of SEQ ID NO: 2, wherein the polypeptide has binding specificity for *Listeria* cells fused to a heterologous polypeptide.

2. The isolated polypeptide of claim 1, wherein the P825Orf2 amino acid sequence is at least 80% identical to the amino acid sequence of SEQ ID NO: 2.

3. The isolated polypeptide of claim 2, wherein the P825Orf2 amino acid sequence is at least 85% identical to the amino acid sequence of SEQ ID NO: 2.

4. The isolated polypeptide of claim 3, wherein the P825Orf2 amino acid sequence is at least 90% identical to the amino acid sequence of SEQ ID NO: 2.

5. The isolated polypeptide of claim 4, wherein the P825Orf2 amino acid sequence is at least 95% identical to the amino acid sequence of SEQ ID NO: 2.

6. The isolated polypeptide of claim 5, wherein the P825Orf2 amino acid sequence is the amino acid sequence of SEQ ID NO: 2.

7. The isolated polypeptide of claim 1, wherein the heterologous polypeptide is a constant domain of an immunoglobulin, a cell wall binding domain, or a secretion signal.

8. The isolated polypeptide of claim 7, wherein the cell wall binding domain is an endolysin, autolysin, or bacteriocin.

9. A nucleic acid comprising a nucleotide sequence encoding the polypeptide of claim 1.

10. An expression vector comprising a nucleic acid sequence encoding a polypeptide comprising a P825Orf2 amino acid sequence at least 75% identical to the amino acid sequence of SEQ ID NO: 2, wherein the polypeptide has binding specificity for *Listeria* cells.

11. A host cell comprising the nucleic acid of claim 10.

12. The host cell of claim 11, wherein the host cell is a bacterial cell, a fungal cell, an insect cell, a plant cell, or an animal cell.

13. The host cell of claim 11, wherein the host cell comprises the encoded polypeptide.

14. An in vitro method for detecting *Listeria* comprising:

(a) contacting a sample suspected of containing *Listeria* with a polypeptide comprising a P825Orf2 amino acid sequence at least 75% identical to the amino acid sequence of SEQ ID NO: 2, wherein the polypeptide has binding specificity for *Listeria* cells; and (b) detecting the *Listeria* bound to the polypeptide.

15. The method of claim 14, wherein the method is further defined as a method of detecting *Listeria* infection in a subject, wherein the sample is obtained from the subject.

16. The method of claim 14, wherein the polypeptide is immobilized on a solid support.

17. The method of claim 14, wherein detecting comprises performing probe hybridization, lateral flow assays, PCR, ELISA, ELFA, enzymatic detection, plasmon resonance, or magnetic bead-based methods.

18. A kit for detecting *Listeria* comprising an isolated polypeptide comprising a P825Orf2 amino acid sequence at least 75% identical to the amino acid sequence of SEQ ID NO: 2, wherein the polypeptide has binding specificity for *Listeria* cells, wherein the polypeptide is immobilized on a solid support.

* * * * *

SEQUENCE LISTING

<160> NUMBER OF SEQ ID NOS: 4

<210> SEQ ID NO 1
<211> LENGTH: 1896
<212> TYPE: DNA
<213> ORGANISM: Bacteriophage P825

<400> SEQUENCE: 1

```
atgactaact atatcatggc aaactcctac gcctttgacg gcacggatga ttttattcat      60
ggcgtttacg aggtagacga acattaact actgttaaga tattacttaa cggaactgat     120
actaacttaa atgcaattgc aggattcact aatgggacaa cctttatggc tgacgtttcc     180
actatcaaat ctcaaatcac attaccaca gtggttacaa tgattatgta taatggaact     240
aaagagcttg cgagatgtcc tgttcctatc tatagccaag ctaatccacc agttccaaaa     300
tcagctgaca gaaaatacac tctagcattg gacttagtta agatactga aaacgtggta      360
```

```
ctaatatccc gcattgctga caaagattta acatccgtat tagttaagct aaccaacaac    420
ggagaagcaa taaacttagt gggacgtacc ccgctatttg agtgtcaatt acccgcacaa    480
acaggtgagt atgctaactt cgtccgtgat gatgggatag caaatggcaa tatgattatt    540
gtagatgccg aacaaggaat cattcaatac aactttgtta agagactttt ctccaaagta    600
ggggctatta acattgccta ttttgcttta gaaacaccag ttggtgatat tgtaaaacgt    660
gtcacaactc gtaactttaa aatcattgta acagatagtg ctattgaagg aaagataaat    720
gctgacgatt acatctctga cattgagtcg cttaaagctg agattgaaat taggcttgct    780
cctgtaattg ctgaaatggt tcaactgaaa gcagatgtgg cagatgctag tgcacagatg    840
gatgagatag aagcactgat tacagctaac caagtaatca aaacagctga tgcagttaac    900
tggcagaaac agaagattac tgatgacaca ggtgccaact tacttacaac tggctcagac    960
acttcaaaag atattcttga tattataaaa acagcaggaa taggtttacg aacattctat   1020
gcagtatcag gtgctgtaaa taacccaacg gctaatactc ctttaagagg aatttctcat   1080
ctaacaacag ctacaaccgg atgggtaatt ggatgggatt cctttggaaa ctcttattca   1140
actttcttaa atggaacagc tggttgggta cttccttgga agagaacgc cacaatgtct   1200
gatgttgcta accaattagc aaccgcagtt tctaccttaa acactagaat ggattccatg   1260
cagaacatcc agctatttga taatagcggt gttcctatag taaatctaga tacggacagt   1320
ggattagata tttacacaga gctaaataaa gttccggctg tatgtatat gacacgaatt   1380
tctggtactg ctggaacaac aaatcctaat actaatgttc ctcctaccac catccgggga   1440
tatacctata ttgaggtaca aggtacttgg gggaatttat atggagtagg ctccaaccag   1500
actatggtaa tgaaccaact aaatagcgga gtgtggcgag gatggagagt gcaagatgca   1560
cgagatactg gctggataaa tatcacagga tttaattctg gatggtcaac tgatgctaca   1620
aaccctccgg catatcgtaa agtaggtaat aaggtttcat tacgtggagt tgttcacatg   1680
gataccgctc taagaaaagg tgttatcgca acacttcctg ctggttatcg tccaatggta   1740
ggtaatcaaa tggttggat atgtgcacgt caaaccactg gtgttaactt tatggcagag   1800
gtttatgtaa gcagtgcagg taacttagag gttgtatgga taaatggtaa cggaacacaa   1860
ggtatttggt taacgccaat agaatttttat attgac                            1896
```

<210> SEQ ID NO 2
<211> LENGTH: 632
<212> TYPE: PRT
<213> ORGANISM: Bacteriophage P825

<400> SEQUENCE: 2

```
Met Thr Asn Tyr Ile Met Ala Asn Ser Tyr Ala Phe Asp Gly Thr Asp
1               5                   10                  15

Asp Phe Ile His Gly Val Tyr Glu Val Asp Glu Thr Leu Thr Thr Val
            20                  25                  30

Lys Ile Leu Leu Asn Gly Thr Asp Thr Asn Leu Asn Ala Ile Ala Gly
        35                  40                  45

Phe Thr Asn Gly Thr Thr Phe Met Ala Asp Val Ser Thr Ile Lys Ser
    50                  55                  60

Gln Ile Thr Leu Thr Thr Val Val Thr Met Ile Met Tyr Asn Gly Thr
65                  70                  75                  80

Lys Glu Leu Ala Arg Cys Pro Val Pro Ile Tyr Ser Gln Ala Asn Pro
                85                  90                  95

Pro Val Pro Lys Ser Ala Asp Lys Lys Tyr Thr Leu Ala Leu Asp Leu
```

```
                100             105             110
Val Lys Asp Thr Glu Asn Val Val Leu Ile Ser Arg Ile Ala Asp Lys
            115                 120                 125

Asp Leu Thr Ser Val Leu Val Lys Leu Thr Asn Asn Gly Glu Ala Ile
130                 135                 140

Asn Leu Val Gly Arg Thr Pro Leu Phe Glu Cys Gln Leu Pro Ala Gln
145                 150                 155                 160

Thr Gly Glu Tyr Ala Asn Phe Val Arg Asp Asp Gly Ile Ala Asn Gly
                165                 170                 175

Asn Met Ile Ile Val Asp Ala Glu Gln Gly Ile Ile Gln Tyr Asn Phe
                180                 185                 190

Val Lys Glu Thr Phe Ser Lys Val Gly Ala Ile Asn Ile Ala Tyr Phe
            195                 200                 205

Ala Leu Glu Thr Pro Val Gly Asp Ile Val Lys Arg Val Thr Thr Arg
            210                 215                 220

Asn Phe Lys Ile Ile Val Thr Asp Ser Ala Ile Glu Gly Lys Ile Asn
225                 230                 235                 240

Ala Asp Asp Tyr Ile Ser Asp Ile Glu Ser Leu Lys Ala Glu Ile Glu
                245                 250                 255

Ile Arg Leu Ala Pro Val Ile Ala Glu Met Val Gln Leu Lys Ala Asp
                260                 265                 270

Val Ala Asp Ala Ser Ala Gln Met Asp Glu Ile Glu Ala Leu Ile Thr
            275                 280                 285

Ala Asn Gln Val Ile Lys Thr Ala Asp Ala Val Asn Trp Gln Lys Gln
            290                 295                 300

Lys Ile Thr Asp Asp Thr Gly Ala Asn Leu Leu Thr Thr Gly Ser Asp
305                 310                 315                 320

Thr Ser Lys Asp Ile Leu Asp Ile Ile Lys Thr Ala Gly Ile Gly Leu
                325                 330                 335

Arg Thr Phe Tyr Ala Val Ser Gly Ala Val Asn Asn Pro Thr Ala Asn
                340                 345                 350

Thr Pro Leu Arg Gly Ile Ser His Leu Thr Thr Ala Thr Thr Gly Trp
            355                 360                 365

Val Ile Gly Trp Asp Ser Phe Gly Asn Ser Tyr Ser Thr Phe Leu Asn
            370                 375                 380

Gly Thr Ala Gly Trp Val Leu Pro Trp Lys Glu Asn Ala Thr Met Ser
385                 390                 395                 400

Asp Val Ala Asn Gln Leu Ala Thr Ala Val Ser Thr Leu Asn Thr Arg
                405                 410                 415

Met Asp Ser Met Gln Asn Ile Gln Leu Phe Asp Asn Ser Gly Val Pro
                420                 425                 430

Ile Val Asn Leu Asp Thr Asp Ser Gly Leu Asp Ile Tyr Thr Glu Leu
            435                 440                 445

Asn Lys Val Pro Ala Gly Met Tyr Met Thr Arg Ile Ser Gly Thr Ala
            450                 455                 460

Gly Thr Thr Asn Pro Asn Thr Asn Val Pro Pro Thr Thr Ile Arg Gly
465                 470                 475                 480

Tyr Thr Tyr Ile Glu Val Gln Gly Thr Trp Gly Asn Leu Tyr Gly Val
                485                 490                 495

Gly Ser Asn Gln Thr Met Val Met Asn Gln Leu Asn Ser Gly Val Trp
            500                 505                 510

Arg Gly Trp Arg Val Gln Asp Ala Arg Asp Thr Gly Trp Ile Asn Ile
            515                 520                 525
```

-continued

```
Thr Gly Phe Asn Ser Gly Trp Ser Thr Asp Ala Thr Asn Pro Pro Ala
    530                 535                 540

Tyr Arg Lys Val Gly Asn Lys Val Ser Leu Arg Gly Val Val His Met
545                 550                 555                 560

Asp Thr Ala Ala Lys Lys Gly Val Ile Ala Thr Leu Pro Ala Gly Tyr
                565                 570                 575

Arg Pro Met Val Gly Asn Gln Asn Gly Trp Ile Cys Ala Arg Gln Thr
            580                 585                 590

Thr Gly Val Asn Phe Met Ala Glu Val Tyr Val Ser Ser Ala Gly Asn
        595                 600                 605

Leu Glu Val Val Trp Ile Asn Gly Asn Gly Thr Gln Gly Ile Trp Leu
    610                 615                 620

Thr Pro Ile Glu Phe Tyr Ile Asp
625                 630

<210> SEQ ID NO 3
<211> LENGTH: 34
<212> TYPE: DNA
<213> ORGANISM: Artificial Sequence
<220> FEATURE:
<223> OTHER INFORMATION: Synthetic primer

<400> SEQUENCE: 3
cgttaggatc catgactaac tatatcatgg caaa                                34

<210> SEQ ID NO 4
<211> LENGTH: 38
<212> TYPE: DNA
<213> ORGANISM: Artificial Sequence
<220> FEATURE:
<223> OTHER INFORMATION: Synthetic primer

<400> SEQUENCE: 4
ggtagcgtcg acttagtcaa tataaaattc tattggcg                            38
```